(12) United States Patent
Bozic et al.

(10) Patent No.: US 11,699,506 B2
(45) Date of Patent: Jul. 11, 2023

(54) METHOD FOR DISTRIBUTION OF A DRUG

(71) Applicant: Biogen MA Inc., Cambridge, MA (US)

(72) Inventors: Carmen Bozic, Newton, MA (US);
Erika M. Gill, Arlington, MA (US);
Anissa Kalinowski, San Francisco, CA (US); Jeffrey K. Francer, Brookline, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 16/784,118

(22) Filed: Feb. 6, 2020

(65) Prior Publication Data
US 2021/0027873 A1     Jan. 28, 2021

Related U.S. Application Data

(60) Division of application No. 15/180,296, filed on Jun. 13, 2016, now abandoned, which is a continuation of application No. 12/376,697, filed as application No. PCT/US2007/075577 on Aug. 9, 2007, now abandoned.

(60) Provisional application No. 60/836,530, filed on Aug. 9, 2006.

(51) Int. Cl.
| | | |
|---|---|---|
| *G16H 10/20* | (2018.01) | |
| *G16H 20/10* | (2018.01) | |
| *G06Q 50/22* | (2018.01) | |
| *G16H 20/00* | (2018.01) | |
| *G06Q 10/083* | (2023.01) | |
| *G16H 10/60* | (2018.01) | |
| *G16H 70/40* | (2018.01) | |

(52) U.S. Cl.
CPC .......... *G16H 10/20* (2018.01); *G06Q 10/083* (2013.01); *G06Q 50/22* (2013.01); *G16H 20/00* (2018.01); *G16H 20/10* (2018.01); *G16H 10/60* (2018.01); *G16H 70/40* (2018.01); *Y02A 90/10* (2018.01)

(58) Field of Classification Search
CPC .............................. G06Q 50/20–26
See application file for complete search history.

(56) References Cited

U.S. PATENT DOCUMENTS

| | | | | |
|---|---|---|---|---|
| 8,527,292 B1* | 9/2013 | Ozden | .................... | G16H 70/60 |
| | | | | 705/30 |
| 2001/0021910 A1* | 9/2001 | Goldstein | .............. | G06Q 40/08 |
| | | | | 705/2 |
| 2002/0052543 A1* | 5/2002 | Williams | ............... | G16H 10/20 |
| | | | | 600/300 |
| 2004/0010425 A1* | 1/2004 | Wilkes | ................... | G16H 20/17 |
| | | | | 705/3 |

* cited by examiner

*Primary Examiner* — Neal Sereboff
(74) *Attorney, Agent, or Firm* — Todd Lorenz

(57) ABSTRACT

A method of providing an anti-VLA-4 antibody to a patient.

21 Claims, 6 Drawing Sheets

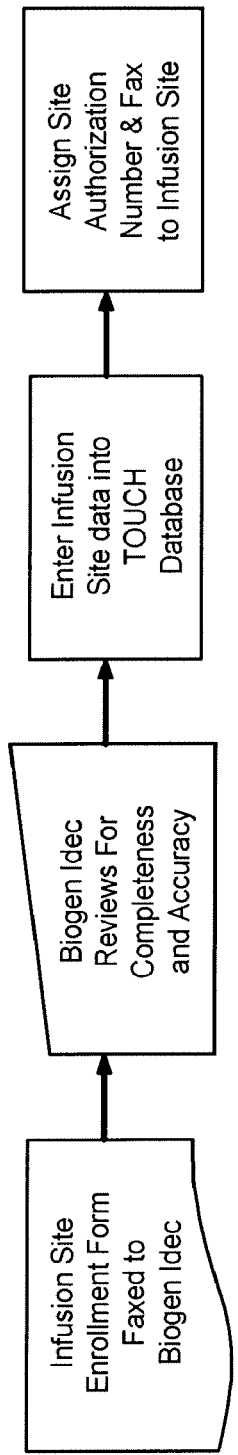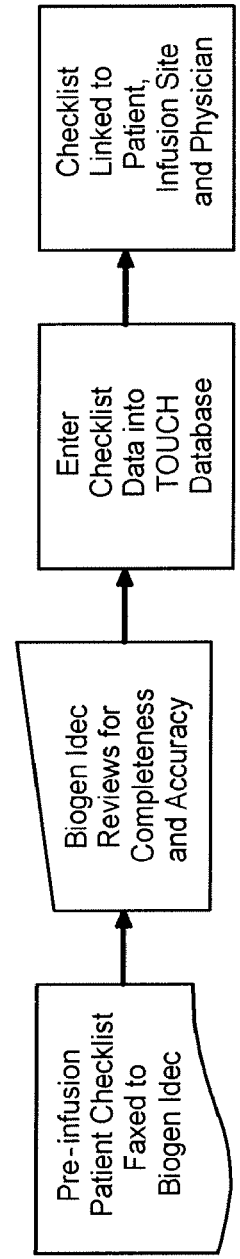

METHOD FOR DISTRIBUTION OF A DRUG

The application is a Divisional of U.S. patent application Ser. No. 15/180,296, filed Jun. 13, 2016, which is a Continuation of U.S. patent application Ser. No. 12/376,697, filed on Mar. 17, 2011, which is a national phase application under 35 U.S.C. § 371 of International Application No. PCT/US2007/075577, filed on Aug. 9, 2007, and claims priority to U.S. Provisional Patent Application No. 60/836,530, filed Aug. 9, 2006. The contents of the aforesaid applications are hereby incorporated by reference in their entirety.

BACKGROUND

The invention relates generally to methods and systems for drug distribution.

SUMMARY

The invention features methods and systems for distributing or providing a therapy, e.g., a drug. The drug can be a VLA-4 blocking agent, e.g., an anti-VLA-4 antibody, e.g., TYSABRI® (natalizumab) or an equivalent or similar antibody. Methods and systems of the invention are particularly useful for drugs which may weaken the immune system. The drug can be administered to treat a patient for a disorder mediated by VLA-4. The drug can be used to treat a patient having multiple sclerosis (MS), Crohn's disease, or a fibrotic condition. In a preferred embodiment the patient has relapsing MS. Methods and systems can include one or more of the steps or elements described herein.

Accordingly, in one aspect, the invention features, a method or system for providing a drug, e.g., an anti-VLA-4 antibody, to a patient, e.g., an MS patient. The system or method includes:

(1) collecting patient and prescriber information, e.g., by providing an enrollment form which includes patient and prescriber information to a central administrator;

(2) reviewing the information, e.g., reviewing an enrollment form which includes the information, entering the information into a system (e.g., a computerized system of one or more computers which can store data, allow data to be retrieved, generate reminders, transmit information and the like), and generating an authorization for treatment of the patient;

(3) communicating the authorization to a treatment site;

(4) conducting (or instructing or authorizing a party to conduct) a treatment site review of a patient which includes gathering medical information about the patient which information is needed to allow administration of the drug, wherein said review can include one or more of:
  i. determining if the treatment site has a current authorization for treatment of the patient;
  ii. confirming that the treatment site does not have notice that the patient is no longer authorized
  iii. providing the patient with information about the drug;
  iv. asking the patient if symptoms have worsened;
  v. asking the patient if he/she has a contraindicated medical condition;
  vi. asking the patient if he/she has taken a contraindicated medication;
wherein an answer of no to iv, v, and vi (or a preselected subset thereof) allows administration of the drug to the patient and an answer of yes to one or more of iv, v, or vi requires the prescriber (or the prescriber's designee) override in order for the drug to be administered; and optionally (5) upon expiration of an authorization obtaining reauthorization for subsequent treatment prior to subsequent treatment, wherein reauthorization can require certification by a prescriber that the subject is qualified to be in the program, e.g., by updating some or all of the information gathered in step 1, or by a prescriber certifying one or more of the following:
  (a) the patient still under his/her care;
  (b) the patient is alive;
  (c) the patient has had no unwanted side effect of the drug, no contraindicated condition, or no contraindicated treatment that the prescriber has not already reported to the central administrator,
provided that if the prescriber reauthorizes the patient must still undergo the review in step (4) prior to receiving the drug.

In a preferred embodiment authorization is necessary but not sufficient for allowing administration of the drug. In a preferred embodiment authorization and satisfaction of treatment site review are sufficient for administration. In a preferred embodiment authorization and satisfaction of treatment site review are necessary but not sufficient for administration.

In a preferred embodiment each shipment of the drug requires that a distributor of the drug obtains a shipment authorization from the central administrator.

In a preferred embodiment the drug is shipped only to and administered only at authorized treatment sites.

In a preferred embodiment central pharmacies that dispense the drug to authorized treatment sites are enrolled in a tracking system.

In a preferred embodiment the central administrator systematically follows and actively solicits information on every patient that receives the drug regarding any adverse events.

In a preferred embodiment a system described herein includes: a user interface for inputting a query; and a processor for generating a query result.

In a preferred embodiment the method or system is applied to at least 50, 100, 500, 1,000, or 10,000 patients.

The invention includes computers, databases, and communication modules configured to implement the methods described herein.

In another aspect, the invention features a method or system for providing a drug, e.g., an anti-VLA-4 antibody to a patient, e.g., an MS patient. The method or system includes one or more of the following steps or elements:

(1) Enrollment of the patient and, optionally, the prescriber in the system. In a preferred embodiment, once the decision to prescribe is made, the prescriber and the patient complete and, optionally, sign or acknowledge, an enrollment form (forms, checklists and other documents referred to herein can individually or collectively be any of electronic, digital, or tangible, e.g., paper). The completed enrollment form is sent to the central administrator.

(2) Review of the enrollment information. The central administrator reviews the completed enrollment form, enters the information from the form into the system (e.g., into a computerized data base and generates an "authorization." The authorization or approval can be, e.g., an electronic or paper "form", e.g., an authorization form.

(3) Communicate information to the treatment center. The authorization, and optionally other information, e.g., from the authorization form generated in (2), is communicated to the treatment site, e.g., an infusion site (as described herein) and to the prescriber, e.g., by sending the authorization form to both by, e.g., facsimile.

(4) Treatment site processing. When the patient arrives at the treatment site, e.g., infusion site, a review is conducted. Indication of the authorization, e.g., an authorization form generated in (2), is necessary but not sufficient to allow treatment. In addition to confirming possession of a current authorization, the treatment site carries out a specific or preselected procedure, in which the patient is screened for eligibility to receive the drug. Thus, in addition to having a current authorization for treatment, a number of issues are resolved before the treatment site can treat the patient. An exemplary treatment site review is as follows:

Before the treatment site can administer the drug, it must check to see if the patient is currently authorized to receive the drug. This can be done by the treatment site referring to the patient's medical record and completing one or more, and preferably all of, the following steps:

(a) If the patient did not receive his or her previous infusion, and physician clearance was required, the treatment site must confirm authorization from the prescriber before providing the current treatment;

(b) Confirm that the treatment site has a current "authorization" on file (if the information, e.g., an authorization form, has been lost, the treatment site can contact the central administer for a replacement form);

(c) Confirm that the treatment site does not have a notice that the patient is no longer authorized, e.g., a Notice of Discontinuation (described herein) or similar form, on file;

(d) Provide the patient with information about the drug, e.g., provide a copy of a Patient Medication Guide (described herein) or a similar guide or information;

(e) An investigation of one or more predetermined matters must be made before treatment. These can include one or more of the following inquiries:

(i) Has the patient had worsening symptoms?

(ii) Does the patient have a contraindicated medical condition, e.g., one that can weaken the immune system? Examples are HIV infection or AIDS, leukemia or lymphoma, or an organ transplant.

(iii) Has the patient taken a contraindicated medication?

If the patient answers "no" to a predetermined set of these inquiries, e.g., "no" to all of them, treatment can proceed. If the patient answers "yes" (or does not know the answer) to a preselected set, e.g., any one of these inquiries, the patient cannot be treated without override by the prescriber (or the prescriber's designee). In this case, the prescriber must be contacted for further instructions. After the treatment site discusses the findings with the patient's prescriber, the prescriber can override and verbally instruct the treatment site to treat the patient.

In a preferred embodiment, the treatment site is required to send the central administrator notice that the procedure was complied with. E.g., any authorization by the prescriber must be documented.

In a preferred embodiment, step (4) includes substeps (b) and (e).

(5) Reauthorization for treatment. The authorization lasts for a maximum of a preselected period. At preselected intervals, the central administrator will send the prescriber a status form, e.g., a Patient Status Report and Reauthorization Questionnaire described herein, or a similar form. This form must be completed and entered into the system for further treatment to occur. Exemplary questions on the status form can include, e.g., one or more of:

(a) Is the patient still under your care?

(b) Is the patient alive?

(c) Does the patient have an unwanted side effect of the drug, a contraindicated condition, or a contraindicated treatment that you have not already reported to the central administrator?

The prescriber must provide answers to these questions and recommend reauthorization for the treatment to continue. If reauthorization is given, the patient would then show up at the treatment site for his/her next treatment and be put through the Treatment Site Processing described in step (4) above.

(6) Controlled distribution system of the drug. Prior to each shipment of the drug, a distributor obtains a shipment authorization from the central administrator. The drug is shipped only to authorized treatment sites, e.g., infusion sites, designated by the central administrator.

(7) Training of treatment sites. The drug is shipped only to and administered only at authorized treatment sites, e.g., infusion sites. Authorized treatment sites are sites that have been trained by the central administrator, e.g., employees of the central administrator, on the known risks, potential benefits and appropriate use of the drug, using educational materials. The treatment sites must agree to comply with, e.g., one or more other requirements described herein. For example, before treatment, the treatment site will complete a checklist, e.g., a pre-treatment checklist described herein, and return the completed checklist to the central administrator, e.g., by mail, facsimile or computer. The central administrator then enters information from the checklist into the system.

(8) Enrollment of central pharmacy. Central pharmacies that dispense the drug to authorized treatment sites are enrolled in a tracking system described herein. Central pharmacies complete an enrollment form, which is returned to the central administrator. The central administrator enters information from the enrollment form into the system, which generates an authorization for the central pharmacy, which includes, e.g., an authorization number and affiliated authorized treatment sites.

(9) Tracking system. The central administrator systematically follows and actively solicits information on every patient that receives the drug regarding any adverse events, e.g., any adverse event described herein. In some embodiments, the central administrator will send a status form to every prescriber for every patient regularly, e.g., every 2, 4, 6, 8, 10 or 12 months. The central administrator will use the status forms to ascertain the vital status of the patient and the occurrence of adverse events and for the prescriber to reauthorize the patient to continue to receive the drug, e.g., for the next 6 months. The central administrator will enter the data from the status forms into the database whenever the central administrator receives a status form.

In a preferred embodiment a system described herein includes: a user interface for inputting a query; and a processor for generating a query result.

In a preferred embodiment the method or system is applied to at least 50, 100, 500, 1,000, or 10,000 patients.

In another aspect, the invention features, a database useful in a method of system described herein, e.g., a database containing one or more of the forms or elements of information described herein, for each of a plurality of patients.

In a preferred embodiment the database is: disposed on tangible medium; disposed on a single unit of tangible medium, e.g., on a single computer, or in a single paper document; provided on more than one unit of tangible medium, e.g., on more than one computer, in more than a single paper document, partly on a paper document and partly on computer readable medium; disposed on computer readable medium; disposed on traditional medium, e.g., paper, which is readable by a human without the use of a computer, e.g., a printed document, chart, table or card catalogue.

All patents, patent applications, and references are hereby incorporated by reference in their entireties. In the case of conflict, the present application controls.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a schematic of an infusion site enrollment process.

FIG. 5 is a schematic of a collection and tracking process for Pre-infusion Patient Checklist data.

DETAILED DESCRIPTION

Enrollment

Figure 1:
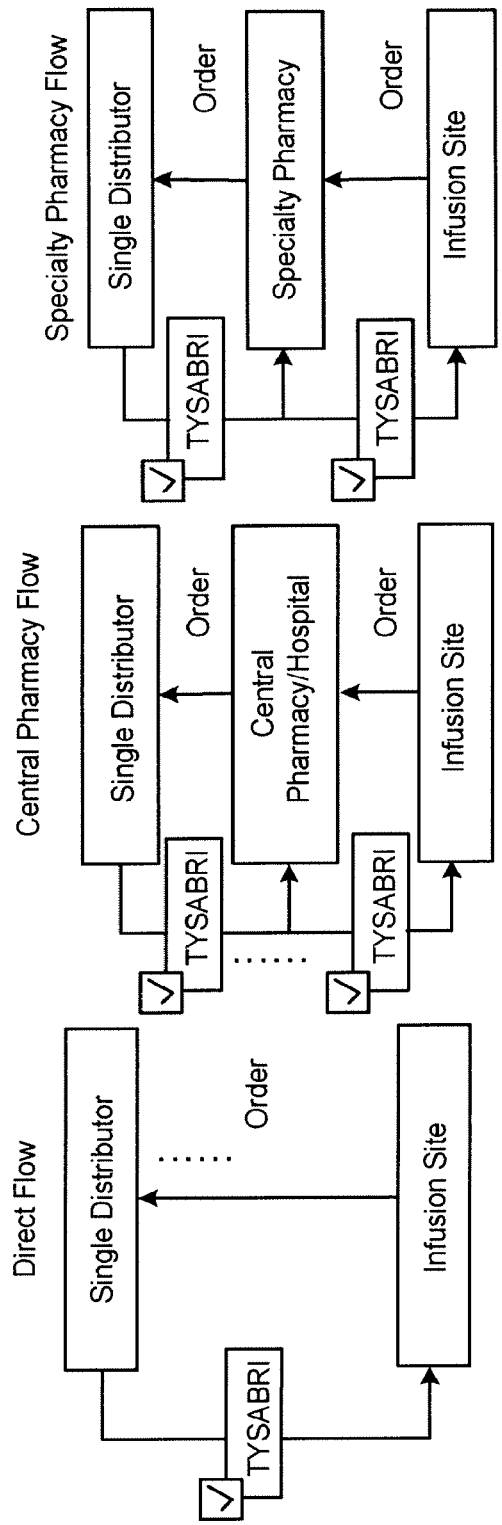
FIG. 1 is a schematic of a TYSABRI® drug distribution process.

In a preferred embodiment, the method includes enrollment of the patient and, optionally, the prescriber, in the system (referred to above as step (1)).

This process can begin with the patient and/or prescriber providing information, e.g., by filling out a form, e.g., a paper or computerized form, e.g., a patient and prescriber form, e.g., the Prescriber/Patient Enrollment Form described herein. Examples of the information collected and of forms that can be used to collect the information are provided herein.

The patient and prescriber form can be supplied by the central administrator and is transmitted, e.g., by mail or computer network, to the prescriber. Both the prescriber and the patient review the form and optionally indicate assent or agreement by signing it (signing can be by traditional indication or electronically). Once the decision to prescribe is made, the prescriber and patient will complete and sign the form. After execution by the patient and the prescriber, the completed form is returned to the central administrator, e.g., by facsimile, computer or mail. Submission of the completed form to the central administrator registers the patient and the prescriber in the system.

In a preferred embodiment, the patient, e.g., an MS patient, attests to one or more conditions set out herein. For example, the patient attests to one or more of the following:

that he/she understands that the drug, e.g., an anti-VLA-4 antibody, e.g., TYSABRI®, is approved for, or only for, a specific condition, e.g., relapsing forms of multiple sclerosis (MS);

that he/she has read a document that provides preselected information on the drug, e.g., the anti-VLA-4 antibody, e.g., TYSABRI® (an example is the Patient Medication Guide for TYSABRI® described herein);

that he/she is aware that the drug, e.g., the anti-VLA-4 antibody, e.g., TYSABRI®, is associated with a preselected risk, e.g., an increased risk of progressive multifocal leukoencephalopathy (PML), which results in an undesirable outcome, e.g., that usually causes disability and/or death and that is untreatable;

that he/she has discussed the risks and benefits of the drug, e.g., the anti-VLA-4 antibody, e.g., TYSABRI®, with his/her physician;

that he/she understands that he/she should call his/her physician promptly to report any continuously worsening symptoms, e.g., those lasting over several days;

that he/she understands that in order to receive the drug, e.g., the anti-VLA-4 antibody, e.g., TYSABRI®, he/she will automatically be enrolled in a registry;

that he/she understands that the patient information described herein may be provided treatment sites, e.g., infusion sites, other administration sites, or pharmacies involved in his/her treatment;

that he/she understands that if he/she does not complete or sign this form, he/she will not be able to receive the drug, e.g., the anti-VLA-4 antibody, e.g., TYSABRI®; and that he/she agrees to bring to each treatment, e.g., TYSABRI® treatment, a list of all medications he/she has taken during the last month.

In a preferred embodiment, the prescriber attests to one or more conditions set out herein. For example, the prescriber attests to one or more of the following:

that he/she will provide the patient, e.g., an MS patient, with information about the drug, e.g., the Patient Medication Guide for TYSABRI® (described herein), will require the patient to read it and will discuss the known risks and potential benefits of the drug, e.g., the anti-VLA-4 antibody, e.g., TYSABRI®, with the patient;

that he/she has read the full prescribing information for the drug, e.g., the anti-VLA-4 antibody, e.g., TYSABRI®;

that he/she is aware that the drug, e.g., the anti-VLA-4 antibody, e.g., TYSABRI®, increases the risk of a preselected disorder, e.g., in the case of TYSABRI®, that TYSABRI® increases the risk of PML, which usually causes disability and/or death and that is untreatable;

that he/she understands that the drug, e.g., the anti-VLA-4 antibody, e.g., TYSABRI®, is indicated for a preselected purpose, e.g., in the case of TYSABRI®, it is indicated as a monotherapy for relapsing forms of MS;

that he/she will promptly report any case of the preselected disorder to the central administrator, e.g., in the case of TYSABRI® treatment, will report any case of PML to the central administrator;

that he/she has discussed the risks and benefits of the drug, e.g., the anti-VLA-4 antibody, e.g., TYSABRI®, and has discussed other therapies, with the patient;

that he/she has confirmed that the patient has the disorder, e.g. a relapsing form of MS, using preselected criteria, e.g., clinical and radiological criteria;

that he/she confirms that the patient has no known contraindications to the drug, e.g., the anti-VLA-4 antibody, e.g., TYSABRI®;

that he/she is not TYSABRI®, is not prescribing any antineoplastic, immunosuppressant, or immunotherapies (other than short courses of corticosteroids) concurrently with TYSABRI®;

that he/she has instructed the patient to promptly report to his/her prescriber any continuously worsening symptoms that persist over several days;

that he/she agrees to provide any information relating to this patient that may be necessary to assess the incidence of risk factors for the preselected disorder (PML in the case of TYSABRI®) and other adverse affects that may be associated with the treatment;

that he/she is able to diagnose and manage the preselected disorder (opportunistic infections and PML in the case of TYSABRI®), or is prepared to refer patients to specialists with these abilities;

that he/she agrees that this patient should be seen and evaluated at a preselected time after the first administration, periodically thereafter for as long as the patient receives the drug, and for at least a preselected number of months after the drug has been discontinued, e.g., in the case of TYSABRI®, agrees that this patient should be seen and evaluated 3 months after the first treatment, 6 months after the first treatment, at least 6 months thereafter for as long as the patient receives TYSABRI®, and for at least 6 months after TYSABRI® has been discontinued;

that he/she will determine at a preselected interval whether this patient should continue on the drug and, if so, authorize treatment for a preselected period, e.g., in the case of TYSABRI® treatment, will determine every 6 months whether this patient should continue on TYSABRI® and if so, authorize treatment every 6 months; and that he/she understands that the patient and the prescriber will be automatically enrolled in the registry.

The form can include a prescription for the drug. E.g., in the case of TYSABRI®, the form can include a preprinted TYSABRI® prescription (1 vial; 12 refills; dose 300 mg; directions: IV infusion per Prescribing Information every 4 weeks). The prescriber has the option of reducing the number of refills and/or the frequency of dosing on the form. It is the TYSABRI® Status Report and Reauthorization Process (described herein) that controls on-going patient re-authorizations, not the number of refills on the prescription.

The patient and prescriber form can also include one or more of the following: baseline demographic information such as the patient's name, contact information, age, gender, and social security number; the prescriber's name; a diagnosis, e.g., in the case of TYSABRI®, a diagnosis of relapsing MS diagnosis; an indication of the most recent prior therapy, e.g., in the case of TYSABRI®, the most recent prior MS therapy; and a summary of prior exposure to the drug, e.g., TYSABRI®.

Review of Enrollment

In a preferred embodiment, the method includes a review of the patient and prescriber form and its entry into the system. This also includes the generation of an "approval" (referred to as step (2) above). E.g., upon receipt at the central administrator, the patient and prescriber form is reviewed, information from it is entered into a computer, and an "authorization form" and unique patient identifier are generated. This is described in the section below.

Upon receipt of the patient and prescriber form, the central administrator assigns a case manager to the patient, e.g., an MS patient. The central administrator confirms that the patient and the prescriber have properly executed the patient and prescriber form (and thereby attested to the items described above). After such confirmation, a data entry person enters information from specific fields on the patient and prescriber form into corresponding fields in a record in the computer. Entry of the correct response into a field is required—if such entry does not occur, the computer will not allow passage to the next field or phase of completion. The case manager may assist the data entry person in this phase. The case manager also matches the patient to a treatment site, e.g., an infusion site (this assignment is based on patient preference and insurance considerations but is not based on any medical consideration or judgment) and confirms that the treatment site is authorized. The computer generates a unique patient enrollment number for the patient. This number remains the same for the patient, even if the patient de-enrolls and subsequently re-enrolls into the program.

A computer record is started for every patient and prescriber form received by the central administrator, even though some patient and prescriber forms may be defective in some way and will not serve to make the patient eligible to receive drug and will not result in the generation of an authorization form, e.g., a Notice of Patient Authorization Form described herein.

The patient and prescriber form may be defective because it lacks a relevant entry, e.g., the signature by the prescriber or patient, or because it includes additional information not requested by the queries on the patient and prescriber form.

The computer generates an authorization, e.g., the authorization form, e.g., the Notice of Patient Authorization Form, if, and only if, all fields on the patient and prescriber form are correctly completed (thus for each field on the patient and prescriber form, the relevant information must be entered into the corresponding "field" in the computer). As discussed above, if a field is not correctly filled out in the computer, the computer will not generate an authorization form, e.g., a Notice of Patient Authorization Form. In this event, the central administrator will notify the prescriber and request a completed patient and prescriber form. The new patient and prescriber form will serve to reinitiate the procedure from the beginning.

The data entry person will follow a standard-operating-procedure for dealing with patient and prescriber forms that include information other than that called for by the patient and prescriber form (e.g., the form includes handwritten or other attached information), referred to herein as "annotated patient and prescriber forms." No approval will be generated for an annotated patient and prescriber form; rather, the prescriber will be contacted and asked that a new properly completed patient and prescriber form be filled out and sent to the central administrator. The new patient and prescriber form will serve to reinitiate the procedure from the beginning.

When all data fields are entered successfully, the computer generates an authorization, e.g., a Notice of Patient Authorization Form. The authorization form can include a computer-generated patient enrollment number.

The computer will include records that correspond to:
(a) completed patient and prescriber forms;
(b) completed patient and prescriber forms where the patient has decided not to go forward with treatment; and
(c) incomplete, annotated or incorrectly answered patient and prescriber forms.

Records in category (c) will not result in the generation of an authorization form, e.g., a Notice of Patient Authorization Form.

In the event that the patient changes prescribers, the patient and new prescriber will be required to complete a new patient and prescriber form. The central administrator will inform the treatment site of the change in prescriber. If the patient does not inform the central administrator of such a change, this will be detected in a status form, e.g., the TYSABRI® Patient Status Report and Reauthorization Questionnaire described herein.

In the event that the patient changes treatment sites, the central administrator will send an authorization form to the new treatment site and a discontinuation notice, e.g., a Notice of Discontinuation Form described herein, to the old treatment site. If the patient does not inform the central administrator of such a change, this will be detected by the central administrator when the new treatment site contacts, e.g., by telephone, the central administrator for approval, e.g., an authorization form, e.g., a Notice of Patient Authorization. The central administrator will update the treatment site data for the patient in the database and will provide an authorization form to the new treatment site.

If a prescriber indicates that a patient is lost to follow up, the central administrator will attempt to contact the patient. If contact is successful and the patient wishes to continue treatment, the patient and the new prescriber must complete a new patient and prescriber form. Otherwise, the central administrator will communicate to the prescriber and to the treatment site that the patient is de-enrolled.

If a patient re-enrolls, the patient and prescriber must submit a new patient and prescriber form.

The Treatment Site

Treatment site processing (referred to as step (4) above) is a critical step in many embodiments of the invention. As will be clear from the following discussion, the patient enrollment number found on the authorization form is necessary but not sufficient to allow treatment. In addition to confirming possession of a current authorization form and a patient enrollment number, the treatment site must carry out a specific procedure, in which a number of issues must be resolved before the treatment site can treat, e.g., treat the patient for MS. These steps are described below. One or more of the following steps can be performed.

The treatment site must confirm enrollment

Before the treatment site can administer the drug, it must check to see if the patient is currently authorized to receive the drug, e.g., the anti-VLA-4 antibody, e.g., TYSABRI®. This is performed by the treatment site's referring to the patient's medical record and completing the following steps:

(a) If the patient did not receive his/her previous treatment, and prescriber clearance was required, the treatment site must confirm authorization from the prescriber before providing the current treatment;

(b) Confirm that it has a current authorization for the patient on file (in the case of TYSABRI®, this is a form which states that the authorization period is 6 months from the first confirmed treatment). If the authorization form has been lost, the treatment site can contact, e.g., by telephone, the central administrator for a replacement authorization form); and (c) Confirm that it does not have a discontinuation notice on file. (If the central administrator learns that a patient is de-enrolled from a status form, e.g., the TYSABRI® Patient Status Report and Reauthorization Questionnaire described herein, or otherwise from the patient, the central administrator sends, e.g., by facsimile, a discontinuation notice to the treatment site. The same information is also telephoned by the central administrator to the treatment site).

The treatment site must provide information about the drug

The treatment site must provide the patient with information about the drug, e.g., written information, e.g., the Patient Medication Guide for TYSABRI® described herein.

The treatment site must conduct predetermined investigations prior to treatment, e.g., the investigations specified on a checklist, e.g., the Pre-infusion Checklist described herein. The checklist requires the treatment site ask the following questions of the patient:

i. Over the past month, have you had any new or worsening medical problems (such as a new or sudden change in your thinking, eyesight, balance, strength or other problems) that have persisted over several days?

ii. Do you have a medical condition that can weaken your immune system, such as HIV infection or AIDS, leukemia or lymphoma, or an organ transplant, that may suggest that you body is not able to fight infections well?

iii. In the past month, have you taken medicines to treat cancer or MS or any other medicines that weaken you immune system? (A list on the reverse side of the checklist is reviewed with the patient.)

iv. In the past month, other than the treatment of a recent relapse, have you taken any of the following medicines: Solu-Medrol®, methylprednisolone, Decadron®, dexamethasone, Depo-Medrol®, prednisone, or other steroid medicines?

The patient must answer "Yes" or "No" to each of these questions. Based on the answers there are three possible outcomes: treatment, no treatment or treatment by prescriber "override".

Treatment Proceeds

If the patent answers "No" to questions 1, 2, 3 and 4 the patient can be treated.

No Treatment or Treatment by Prescriber "Override"

If the patent answers "Yes" (or does not know the answer) to any of 1, 2, 3, or 4 the patient cannot be treated without override by the prescriber (or the prescriber's designee). If the answer to any of these questions is "Yes", the prescriber must be contacted for further instructions. After the treatment site discusses the findings with the patient's prescriber, the prescriber can override and verbally instruct the treatment site to infuse.

The treatment site is required to send the central administrator a copy of the completed checklist, e.g., the Pre-infusion Checklist described herein. Any authorization by the prescriber must be documented. This will let the central administrator know if the patient was treated. The checklist will go into the database and be part of the patient's record in the database. In some embodiments, the checklist can be computerized, e.g., web-based, for electronic transmission to or electronic access by the central administrator.

If a treatment site does not comply with these requirements, the central administrator will send a warning letter to the treatment site. In the event of continuing non-compliance, the central administrator will de-list the treatment site and move the patients elsewhere.

Reauthorization

In a preferred embodiment, the method includes reauthorization for continued treatment, e.g., treatment of MS. For example, the approval provided by the authorization form can last for a maximum of six months. At six month intervals, the central administrator will send, e.g., by facsimile, the prescriber a status form, e.g., the TYSABRI® Patient Status Report and Reauthorization Questionnaire described herein.

The prescriber is expected to complete the status form and to return it to the central administrator, e.g., by mail or facsimile. The information from the completed status form will be entered into the computer. In some embodiments, the status form can be computerized, e.g., web-based, for electronic transmission to or electronic access by the central administrator. If the prescriber does not make a timely reply, the central administrator will send two facsimiles and make multiple telephone calls to the treatment site.

The status form, e.g., the TYSABRI® Patient Status Report and Reauthorization Questionnaire, will ask the following:

A. Is the patient still under your care?
B. Is the patient alive?
C. Does the patient have a preselected disorder, e.g., PML, that you have not already reported to the central administrator?
D. Has the patient been hospitalized for a contraindicated condition, e.g., an opportunistic infection that you have not already reported to the central administrator?
E. Is the patient currently receiving or has the patient received contraindicated treatment, e.g., intermittent steroids for the treatment of MS relapse within the last 6 months? (If "Yes", how many steroid treatments?)
F. Is the patient currently receiving or has the patient received any immunomodulatory or immunosuppressant products in the previous 6 months? (If "Yes", indicate the specific drug and the number of uses.)
G. Do you reauthorize treatment for the next 6 months?

If the answer to Question A is "No", the central administrator will send a new patient and prescriber form or will initiate the steps to discontinue the patient from treatment.

If the answer to Question C or D is "Yes" or "Under investigation", the central administrator will contact the prescriber to obtain information If the answer to Question G is "No", the central administrator will contact, e.g., by telephone, the treatment site, the patient, and the prescriber and make sure they know the patient is de-enrolled. The central administrator will also send a discontinuation notice, e.g., a Discontinuation Notification Form described herein, to the treatment site, the patient and the prescriber.

If the answer to Question G is "Yes", and the answers to Questions C and D are "No", the central administrator will send a new authorization form to the patient, the prescriber and treatment site. The patient would then show up at the treatment site for his/her next treatment and be put through the treatment site process described in step (4) above.

Controlled Distribution System

In a preferred embodiment, the method includes a controlled distribution system for the drug, e.g., TYSABRI® (referred to as step (6) above) to treat MS. Under the controlled distribution system, distributors and pharmacies (e.g., specialty and central pharmacies described herein) will each be associated with authorized treatment sites. The distributors will sell the drug, e.g., the anti-VLA-4 antibody, e.g., TYSABRI®, to customers, but will ship the drug only to authorized pharmacies (e.g., specialty and central pharmacies) or treatment sites. The distributors or specialty pharmacies will ship the drug, e.g., the anti-VLA-4 antibody, e.g., TYSABRI®, only to authorized treatment sites or their affiliated central pharmacy designated by the central administrator. The distributors or specialty pharmacies must obtain shipment authorization, e.g., a shipment authorization code, from the central administrator prior to each shipment.

In a preferred embodiment, the method includes only a single distributor.

In a preferred embodiment, the treatment site receives drug from one the following:

1. Directly from a distributor, which first obtains a shipment authorization from the central administrator, which then delivers the drug from its warehouse to the treatment site;
2. From a central pharmacy (described herein), which would obtain the drug from a distributor. The distributor first obtains a shipment authorization from the central administrator and then delivers the drug from its warehouse to the central pharmacy. The central pharmacy then dispenses the drug directly to the authorized treatment site; or
3. From a specialty pharmacy (described herein), which would obtain the drug from a distributor. The distributor first obtains a shipment authorization from the central administrator and then delivers the drug from its warehouse to the specialty pharmacy. The specialty pharmacy would then obtain a shipment authorization from the central administrator to dispense the drug to the treatment site.

Treatment Site Training

In a preferred embodiment, the method includes training of the treatment site, e.g., by the central administrator, relevant to the treatment of MS with the drug. Prior to treatment site authorization, the central administrator will provide training, e.g., on the known risks, potential benefits, and appropriate use of the drug, e.g., the anti-VLA-4 antibody, e.g., TYSABRI®. The central administrator can use training materials, e.g., educational materials on the drug and/or its administration. The central administrator will instruct the treatment sites to report adverse events to the central administrator. In preferred embodiments, the treatment sites will be required to distribute information about the drug, e.g., the TYSABRI® Medication Guide described herein, and to conduct one or more of a predetermined set of queries prior to treatment, e.g., to complete a pre-treatment checklist, e.g., a Pre-infusion Patient Checklist described herein. The treatment site will then send, e.g., by mail, facsimile, or computer, the completed pre-treatment checklist to the central administrator, e.g., within 4, 8, 12, 24, 48, or 72 hours of the patient's visit, regardless of whether the drug was administered.

In some embodiments, the central administrator enters into the computer database information from the checklist, and the information will be linked to the patient, treatment site and prescriber data in the database. The central administrator will contact the treatment site, e.g., by telephone, to follow-up on incomplete or illegible checklists. If a treatment site does not comply with these requirements, the central administrator will send a warning letter to the treatment site. In the event of continuing non-compliance, the central administrator will de-list the treatment site and move the patients elsewhere, e.g., to another treatment site.

Central Pharmacies

In some embodiments, the method includes enrollment of central pharmacies (referred to as step (8) above). As described herein, central pharmacies are located within, e.g., a hospital, group practice or treatment site, and are affiliated with a treatment site. Central pharmacies store drug inventory and release it to a treatment site locally.

The central administrator will provide training to central pharmacies by providing educational materials, e.g., on the distribution system and inventory. The central pharmacy will complete an enrollment form, e.g., the Central Pharmacy Enrollment Form described herein, and return it to the central administrator. The central administrator will enter the information from the enrollment form into the computer database, at which time an authorization number, e.g., a site authorization number described herein, is assigned to the central pharmacy. The central administrator will send, e.g., by facsimile or computer, an authorization, e.g., a site authorization form, e.g., a Site Authorization Confirmation described herein, to the central pharmacy. The site authorization form includes an authorization number and a list of affiliated authorized treatment sites.

Tracking

In some embodiments, the method provides for systematic tracking of all drug-treated patients. The central administrator will systematically follow and actively solicit information regarding the occurrence of any adverse event (e.g., PML and other serious opportunistic infections in the case of TYSABRI®) through a variety of mechanisms on every drug-treated patient in the US. For example:

- Through periodic collection, e.g., weekly, monthly, or semi-annually, of pre-treatment checklists described herein, the central administrator will track drug dosing on an up-to-date, individual patient basis.
- On the mandatory patient and prescriber form described herein, prescribers must attest to report to the central administrator any case of an adverse event (in the case of TYSABRI®, PML, other serious OI, or death).
- On the mandatory patient and prescriber form, patients must attest that they will report to their prescriber any new or worsening symptoms that last several days, especially nervous symptoms. The drug information, e.g., the TYSABRI® Medication Guide, also provides these instructions to the patient. If the prescriber determines that the symptoms are related to PML (in the case of TYSABRI®), then the prescriber is obligated to report the case to the central administrator.
- For additional diligence, the central administrator will actively query prescribers, e.g., every 1 month, e.g., every 2, 3, 4, 5, 6, 8, 10 or 12 months, on each of their patients regarding the occurrence of an adverse event (in the case of TYSABRI®, PML, other serious OI, or death) using a status form, e.g., the TYSABRI® Patient Status Report and Reauthorization Questionnaire described herein. If a patient discontinues treatment, the central administrator will actively follow-up on the status of such a patient.

In some embodiments, the central administrator will send a status form, e.g., a TYSABRI® Patient Status Report and Reauthorization Questionnaire, to every prescriber for every patient regularly, e.g., every 2, 4, 6, 8, 10 or 12 months. The central administrator will use the status forms to ascertain the vital status of the patient and the occurrence of adverse events (e.g., PML or other serious OI in the case of TYSABRI®), and for the prescriber to reauthorize the patient to continue to receive the drug, e.g., for the next 6 months. For example, prescribers will be asked whether the patient is still under their care, whether the patient is alive, whether the patient has a diagnosis of PML or has been hospitalized for an opportunistic infection. In addition, the status form will ask whether the patient is receiving or has received within, e.g., the last 6 months any immunomodulatory or immunosuppressant therapies, whether the patient is currently or has received within, e.g., the last 6 months any systemic steroids, whether the patient has received intermittent steroids within, e.g., the last 6 months, and whether the prescriber is authorizing the continuation of drug treatment in this patient, e.g., for the next 6 months. The central administrator will send the status form to the prescriber, e.g., via facsimile, mail or computer, who will be expected to complete and return it to the central administrator, e.g., by facsimile, mail or computer. The central administrator will enter the data from the status forms into the database whenever the central administrator receives a status form.

The prescriber must reauthorize drug treatment for the patient, e.g., every 6 months using the status form, e.g., the TYSABRI® Patient Status Report and Reauthorization Questionnaire. All data fields on the status form must be completed and the answers appropriate. In addition, the prescriber must authorize the continuation of the drug in order for the patient to continue to receive drug treatment.

An appropriately completed status form is a requirement for the patient to continue to receive drug treatment. In order for the prescriber to be able to complete this status form, the central administrator expects that the prescriber will have recently examined the patient. By requiring reauthorization for drug use through the use of this status form, the central administrator helps to facilitate close clinical follow-up of the patient by his/her prescriber, including patient-prescriber visits, e.g., every 6 months. Upon reauthorization, an authorization form, e.g., a Notice of Patient Authorization described herein, will be sent to the prescriber and the treatment site with the new patient authorization period. Treatment site personnel will confirm that the patient is currently authorized prior to every treatment.

In a preferred embodiment, the central administrator will follow steps to determine whether a patient may have discontinued drug treatment. These include:

- A prescriber may complete send to the central administrator, e.g., by facsimile or computer, a form to discontinue the patient.
- Through monthly collection of pre-treatment checklists, e.g., Pre-Infusion Patient Checklists, the central administrator will track drug dosing on an individual patient basis. By diligently following-up on any missing pre-treatment checklists, the central administrator will identify any patient who has discontinued drug treatment.
- The central administrator will identify patient discontinuations through the status form, e.g., the TYSABRI® Patient Status Report and Reauthorization Questionnaire (e.g., if the prescriber does not authorize the continuation of drug treatment).
- The central administrator may also confirm patient discontinuations through spontaneous reporting by the patient, prescriber, or treatment site.

EXAMPLES

Example 1

Controlled Distribution of TYSABRI® for Relapsing MS

The following example describes a plan for the controlled distribution of TYSABRI® by Biogen Idec. Although the plan refers to Biogen Idec as the central administrator, it is applicable to any central administrator. Although the plan refers to TYSABRI®, the plan can be adapted to other drugs. Although the following plan includes many features, a plan may include all or a subset of these features as needed for a particular application.

1. Risk Management Plan Background

1.1 Overview

Biogen Idec (the Sponsor) has developed a comprehensive risk management plan (RiskMAP), consisting of both risk assessment and a risk minimization features. This document outlines the goals, objectives, and processes of the revised TYSABRI® RiskMAP based on discussions with the Agency and the recommendations of the Peripheral and Central Nervous System Drugs Advisory Committee (Advisory Committee). The TYSABRI® RiskMAP is designed to promote informed risk-benefit decisions between prescribers and patients regarding the use of TYSABRI® in relapsing multiple sclerosis (MS), to minimize morbidity and mortality due to progressive multifocal leukoencephalopathy (PML) through early detection with clinical vigilance, and to minimize the risk of PML by treating patients who are not immunocompromised and, consistent with the Prescribing Information (PI), warning against concurrent use with antineoplastics, immunosuppressants or immunomodulators, such as beta-interferons or glatiramer acetate. In addition, the plan seeks to determine the incidence and risk factors for PML and other serious opportunistic infections (OI) in patients treated with TYSABRI®, as well as the overall safety of TYSABRI® in the clinical practice setting.

This plan has been developed in collaboration with the FDA, in consideration of FDA's Guidance Document on this topic, and in consideration of the deliberations of the Advisory Committee. In addition, the Sponsor sought extensive feedback from neurologists to obtain their recommendations on how best to minimize the risk of PML, and surveyed many neurologists, MS patients, infusion nurses, infusion sites, and central pharmacies regarding the feasibility of the plan. Biogen Idec has also developed a companion Quality Plan that outlines the monitoring of systems and compliance data generated by the RiskMAP.

The TOUCH (TYSABRI® Outreach: Unified Commitment to Health) Prescribing Program (Table 1) features, among other things:

- Mandatory enrollment of all prescribers and patients into the TOUCH Prescribing Program, a registry that provides diligent safety surveillance and systematic tracking of all patients
- Mandatory training and enrollment of all infusion sites, and all central pharmacies affiliated with authorized infusion sites, into the TOUCH Prescribing Program.
- Controlled distribution system for TYSABRI® so that TYSABRI® is delivered to and administered only in authorized infusion sites
- Mandatory completion of the Pre-Infusion Patient Checklist and distribution of the Medication Guide to each patient prior to each monthly TYSABRI® dose
- Real-time submission of Pre-Infusion Patient Checklists to Biogen Idec to monitor infusion site compliance and to track TYSABRI® dosing on a patient-specific basis
- Mandatory prescriber re-authorization of TYSABRI® dosing for each patient every 6 months
- At the heart of the TOUCH Prescribing Program is an integrated, computerized, validated database that captures enrollment, patient tracking, and drug distribution data.

TABLE 1

| TOUCH Program Elements | |
|---|---|
| ENROLLMENT | TRACKING |
| Patients | Pre-Infusion Patient Checklists |
| Physicians | Patient Status Report and |
| Infusion Sites | Reauthorization Questionnaires |
| Central Pharmacies | Patient Discontinuation Questionnaires |
| Single Distributor | Follow-Up of Checklists and |
| ≤12 Specialty Pharmacies | Questionnaires |

The RiskMAP primarily seeks to minimize the risk of PML, a rare, but serious, adverse event without creating unintended consequences that may obstruct appropriate patient access to the potential significant benefits of TYSABRI®. Once implemented, Biogen Idec will continue to assess the effectiveness of the RiskMAP and the information that it generates through a multi-disciplinary TYSABRI® Risk Management Review Committee, report the outcomes to FDA, and act promptly to revise and improve the plan, as necessary, in order to achieve its goals.

1.2 Risk Management Goals

In consideration of FDA's risk management guidance document, the TYSABRI® RiskMAP incorporates both risk minimization and risk assessment goals. The goals of risk minimization are:

To promote informed risk-benefit decisions regarding TYSABRI® use in MS patients. Prescribers and their patients should know that TYSABRI® is associated with an increased risk of PML, which usually causes death or severe disability. Prescribers should also know that TYSABRI® is indicated only for the treatment of relapsing MS.

To minimize the risk of PML. To the extent possible, based on currently available data, patients who are already at risk of developing PML should not receive TYSABRI® treatment. Patients who are immunocompromised are at increased risk of developing PML and, consistent with the PI, generally should not receive TYSABRI® treatment. In addition, based on limited data, use of TYSABRI® in combination with antineoplastic, immunosuppressant or immunomodulatory agents may further increase the risk of PML compared to TYSABRI® monotherapy. Thus, prescribers should know that TYSABRI® should not be used concurrently with antineoplastics, immunosuppressants or immunomodulators.

To minimize death and disability due to PML. Although the data are limited, it is prudent to encourage early detection and immune-reconstitution in any patient who develops PML in order to potentially improve patient outcome. Thus, it is important that prescribers know how to diagnose PML and know to withhold TYSABRI® dosing immediately at the first signs or symptoms suggestive of PML. Patients should know to promptly report to their prescriber any continuously worsening nervous system symptoms lasting over several days.

The goals of risk assessment are:

To determine the incidence and risk factors for PML and other serious opportunistic infections with TYSABRI® treatment. Safety data from the TOUCH Prescribing Program will support this goal, as will data from a long-term observational study (TYSABRI® Global Observational Program in Safety [TYGRIS]).

To assess further the overall safety profile of TYSABRI®. Biogen Idec will continue to study the safety profile of TYSABRI® beyond 2 years of dosing and in the clinical practice setting, the nature and incidence of rare unanticipated adverse events, and the effect of TYSABRI® on humoral and cell-mediated immunity. Safety data from the TOUCH Prescribing Program, TYGRIS, and TYSABRI® clinical trials will support this goal.

1.3 Important Features of Medical Management of MS Patients

There are several important aspects about the medical management of patients with MS and the administration of TYSABRI® that allow for successful implementation of the Risk Minimization Action plan (RiskMAP).

1. TYSABRI® is Prescribed by Prescribers who Specialize in the Care of Patients with MS.

In the United States, patients with MS receive medical treatment by a relatively small group of physicians, primarily neurologists. Approximately 6,000 physicians treat 90% of patients with MS. This is in contrast to 170,000 family practitioners that treat primary care diseases in the US. Biogen Idec has a dedicated force of physicians and sales representatives that interact with neurologists and other healthcare professionals who care for patients with MS. Consequently, Biogen Idec can readily reach nearly all prescribers who are expected to prescribe TYSABRI®.

Because PML is a disease of the central nervous system, the targeted prescribers of TYSABRI® are also the best-qualified physicians to diagnose and manage PML. Neurologists have the expertise to monitor subjects for signs and symptoms indicative of PML and select appropriate diagnostic tests to diagnose a patient with PML.

2. Patients with MS are Knowledgeable about their Treatment Options.

Patients with MS are generally a young, highly motivated patient population. In a recent survey, 94% to 99% of patients with MS were aware of their treatment options, including beta-interferons and glatiramer acetate (GA) (Biogen Idec, data on file). During the period when TYSABRI® was available commercially, Biogen Idec found that 79% of patients with MS were aware of the introduction of TYSABRI®. Also, Biogen Idec has sought feedback from patients with MS and found that the potential risk of PML with TYSABRI® has been broadly disseminated in the MS community. Based on Biogen Idec's market research, patients with MS want to learn more about the risks of PML with TYSABRI®.

3. Discussion of Risks and Benefits Associated with MS Treatment is the Standard of Care in Neurology Practice.

Prescribing a disease-modifying treatment for a serious, disabling disease such as MS is a carefully considered and deliberate decision. Based upon feedback from neurologists and MS patients, this decision usually involves a detailed discussion between the prescriber and patient about the risks and benefits of available therapies. Some neurologists already use an informed-consent form prior to initiating therapy with an immunomodulatory agent such as interferon-beta or glatiramer acetate. The TYSABRI® risk minimization strategy builds upon this existing decision-making process.

4. TYSABRI® is Administered Monthly by Healthcare Professionals in Infusion Sites.

In contrast to therapies that are self-administered in the patient's home, TYSABRI® is administered intravenously every month at an infusion site under the care and management of infusion nurses. This regulated, procedure-oriented dispensing environment allows for monthly monitoring of patients for potential symptoms suggestive of PML and for effective dissemination of information on TYSABRI® that reinforces appropriate use.

The TOUCH Prescribing Program is designed to inform prescribers, infusion nurses, and MS patients about the risk of PML and how to minimize that risk. A RiskMAP system of mandatory enrollment of all prescribers and patients, controlled distribution of TYSABRI®, and administration of TYSABRI® only in trained and authorized infusion sites was developed to build upon the unique aspects of the medical management of MS patients and the administration of TYSABRI®.

2. Controlled Distribution System for TYSABRI®

Biogen Idec and Elan have designed a controlled distribution system to deliver TYSABRI® only to infusion sites (or, if appropriate, their affiliated central pharmacies) that have been trained by Biogen Idec or Elan personnel on the known risks and appropriate use of TYSABRI®, using education tools[1], and have attested that they will follow the RiskMAP requirements (See Section 4.2 and 4.3). The controlled distribution of TYSABRI® will allow Biogen Idec and Elan to track TYSABRI® shipments, i.e., the location and number of vials shipped to infusion sites and central pharmacies.

[1] As requested by the FDA, prior to distributing education materials relating to the RiskMAP, the Sponsor shall submit them for FDA review.

2.1 Distribution System Description

Under the controlled distribution plan, a single distributor, specialty pharmacies, and central pharmacies will each be associated with authorized infusion sites. Elan has contracted with a single distributor and will contract with a limited number of specialty pharmacies (≤12) to distribute TYSABRI® only to authorized infusion sites. The single distributor will sell TYSABRI® to its customers, but only ship product to authorized specialty pharmacies, central pharmacies or infusion sites.

The single distributor and participating specialty pharmacies will be contractually obligated to follow RiskMAP requirements in order to purchase and distribute TYSABRI®. The contracts will specify, among other requirements, that:

TYSABRI® will be shipped only to authorized infusion sites (or their authorized affiliated central pharmacy) designated by Biogen Idec and Elan, either directly from the single distributor or through one of the specialty pharmacies.

A shipment authorization code must be obtained from Biogen Idec and Elan for each shipment prior to each shipment.

Specialty pharmacy providers are organizations that dispense specialty products, including injectable and infusible therapies. Product is labeled with the patient's name, and is typically dispensed directly to an authorized infusion site (e.g., physician's office or other infusion site).

Central pharmacies are distinct from specialty pharmacies. A central pharmacy is located within a hospital, group practice or infusion site, and is affiliated with an infusion site. The central pharmacy is responsible for purchasing, storing, and dispensing product to its affiliated infusion site. Biogen Idec will provide each authorized central pharmacy with a list of the authorized infusion sites to which it may release product. The central pharmacy may only dispense product to these authorized sites and must maintain a TOUCH Central Pharmacy Inventory Tracking Log. This log is meant to document each instance TYSABRI® is released by the central pharmacy, including the number of vials released and the infusion site (including its unique Site Authorization Number) that received the product. The Central Pharmacy should retain its Inventory Tracking Logs for 5 years.

2.2 Distribution System Process

The TYSABRI® shipment and authorization process is illustrated in FIG. 1. There are three ways in which an infusion site can receive product. A shipment authorization is required prior to shipment in each of these cases.

1. Infusion site obtains product directly from the single distributor. The single distributor would obtain a shipment authorization from Biogen Idec and Elan, and deliver TYSABRI® directly from the single distributor warehouse to the infusion site.

2. Infusion site utilizes an affiliated central pharmacy. The central pharmacy would obtain TYSABRI® from the single distributor. The single distributor would obtain a shipment authorization from Biogen Idec and Elan, and deliver TYSABRI® directly from the single distributor warehouse to the central pharmacy. The central pharmacy will then dispense TYSABRI® directly to the authorized infusion site.

3. Infusion site obtains TYSABRI® from a specialty pharmacy. The specialty pharmacy would obtain TYSABRI® from the single distributor. The single distributor would obtain a shipment authorization from Biogen Idec and Elan, and deliver TYSABRI® directly from the single distributor warehouse to the specialty pharmacy. The specialty pharmacy would then obtain a shipment authorization from Biogen Idec and Elan to dispense TYSABRI® to the infusion site.

2.3 Shipment Authorization

Biogen Idec and Elan will permit TYSABRI® delivery only to authorized infusion sites and only in quantities justified by the number of authorized patients at the site. Biogen Idec will maintain the list of authorized sites (authorized infusion sites and authorized central pharmacies) in the TOUCH database as described in Sections 4.4 and 5.2. An acceptable order quantity will be established on a site-by-site basis taking into account the amount of drug previously shipped to the site relative to the confirmed and expected demand from enrolled patients at the site.

Figure 2:
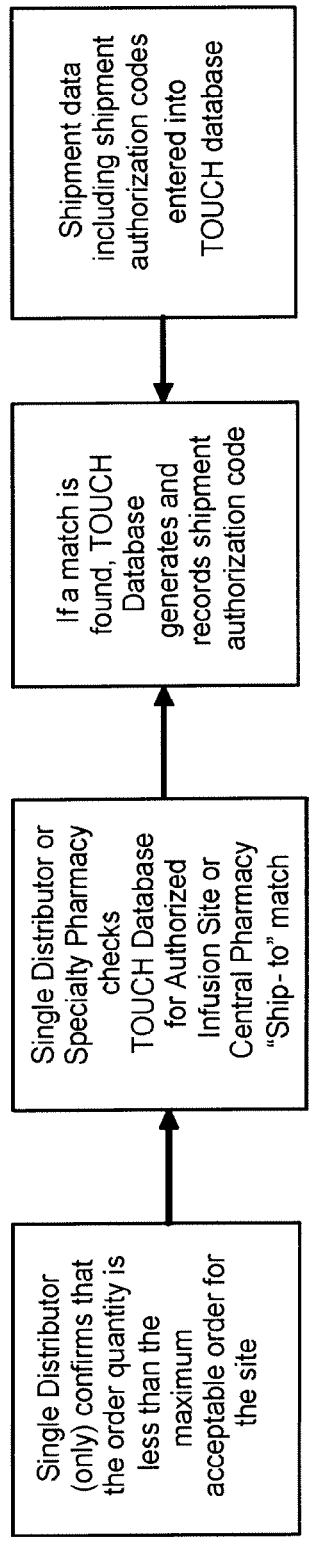
FIG. 2 is a schematic of a shipping authorization process.

As described in FIG. 2, when the single distributor receives an order from an infusion site, the single distributor would first confirm that the order quantity is less than the maximum acceptable order for that site. Then, the single distributor will access the TYSABRIdirect.com web site and enter the infusion site or central pharmacy address that TYSABRI® will be shipped to. The web site will access the TOUCH database and if the "ship to" address that the single distributor entered matches an authorized infusion site (or affiliated authorized central pharmacy), a shipment authorization code will be provided to the central distributor and will be captured in the TOUCH database. Specialty pharmacies follow the same process of authorization based on the "ship to" address, but are not required to confirm order quantity because they only dispense on a per patient basis. The single distributor and SPPs must not ship TYSABRI® without a shipment authorization code.

2.4 Shipping Data Provided by Single Distributor and Specialty Pharmacies

The single distributor and specialty pharmacies will be required to provide shipment authorization codes as well as other information critical to monitoring shipments to authorized infusion sites and inventory levels on a weekly basis to Biogen Idec and Elan, including:

Central Distributor information: unique identifier, name, invoice number, location shipped from SPP information: unique identifier, name, location shipped from Shipment information: quantity shipped, quantity returned, date Ship-to information: identifier, name, address, class of trade Shipment authorization code: as obtained from TOUCH database for each shipment

2.5 Reconciliation of Shipping Addresses and Quantities

Biogen Idec and Elan will reconcile the shipping addresses that have received TYSABRI® shipments against the list of authorized sites on an on-going basis. Biogen Idec will reconcile, at least monthly, the amount of drug shipped to each site compared to the expected volume of infusions for that site. These site reconciliations will be conducted by analyzing beginning inventory balances, product shipped during the reconciliation period, product returns, and the number of confirmed patient infusions. Any discrepancies identified by this reconciliation would be flagged for further investigation. Such investigations could include for-cause audits of physical inventory on an as-needed basis to confirm that the calculated inventory level at a site is consistent with the actual inventory level. This combination of ongoing reconciliation and follow-up investigations is intended to enable management of low inventory levels across the distribution system.

Reconciliations will also be performed with central pharmacy data. Product shipped into the Central Pharmacy will be reconciled against confirmed infusions of authorized patients at the affiliated authorized infusion sites, at least monthly. In addition, Biogen Idec will examine a sample of inventory tracking logs and reconcile them with shipping data to measure central pharmacy compliance.

3. Mandatory Enrollment of Prescribers and Patients

A key feature of the RiskMAP is mandatory enrollment of all prescribers and patients into the TOUCH Prescribing Program as a prerequisite to prescribing or receiving TYSABRI® treatment.

3.1 Prescriber/Patient Enrollment Form

Prescribers and patients must complete and sign a mandatory Prescriber/Patient Enrollment Form and send it to Biogen Idec prior to initiating TYSABRI® treatment.

The purpose of the Prescriber/Patient Enrollment Form is to help assure that (1) both the prescriber and patient are informed of the known risks of TYSABRI®, including the risk of PML, (2) TYSABRI® is prescribed only for appropriate patients, and (3) that patients will be tracked longitudinally for safety outcomes.

The Prescriber/Patient Enrollment Form will be used to collect baseline demographic information including the prescriber's name and contact information, patient's name, contact information, age, gender, social security number, relapsing MS diagnosis, most recent prior MS therapy; prior TYSABRI® exposure; a TYSABRI® prescription; and a Patient-Prescriber Acknowledgement.

The TYSABRI® prescription is pre-printed as a 300 mg dose to be administered by IV infusion every 4 weeks, with 12 refills/doses. The prescriber has the option of reducing the number of refills and/or the frequency of dosing on the Enrollment form. Prescribers are able to de-enroll patients at any time, notwithstanding the number of refills indicated on this prescription. It is the TYSABRI® Status Report and Reauthorization process (described in Section 6.3 and 6.4) that controls on-going patient re-authorizations, not the number of refills on the prescription.

Biogen Idec will require that, prior to starting TYSABRI® treatment, the prescriber will provide the patient with the TYSABRI® Medication Guide, will require the patient to read it, and will discuss the known risks and potential benefits of TYSABRI® with the patient. Once the decision to prescribe TYSABRI® is made, the prescriber and patient will complete and sign the Prescriber/Patient Enrollment Form. The completed and signed Enrollment Form must be faxed to Biogen Idec before the prescriber may prescribe TYSABRI® and the patient may receive an infusion. Biogen Idec will have mail and fax options to send and receive forms. By signing the Enrollment Form, the patient and the prescriber acknowledge the following:

Patient Acknowledgement

I acknowledge that:

TYSABRI® is a medicine approved only to treat patients with relapsing forms of multiple sclerosis (MS).

- TYSABRI® is generally recommended for patients who have not been helped enough by, or cannot tolerate other treatments for MS
- I have talked to my doctor and understand the benefits and risks of TYSABRI® treatment
- TYSABRI® increases your chance of getting a rare brain infection that usually causes death or severe disability.
- This infection is called progressive multifocal leukoencephalopathy (PML). PML usually happens in people with weakened immune systems
- No one can predict who will get PML. There is no known treatment, prevention, or cure for PML
- My chance for getting PML may be higher if I am also being treated with other medicines that can weaken my immune system, including other MS treatments.
- Even if I use TYSABRI® alone to treat my MS, it is not known if my chance for getting PML will be lower. It is also not known if treatment for a long period of time with TYSABRI® can increase my chance for PML
- I should call my doctor right away if I get any new or worsening symptoms that last several days, especially nervous system symptoms. Some of these symptoms include a new or sudden change in my thinking, eyesight, balance, or strength, but I should also report other new or worsening symptoms
- To receive TYSABRI®, all patients must be authorized in a special program called the TOUCH Prescribing Program.
- The TOUCH Prescribing Program is run by the company that makes TYSABRI®. The company will collect information about my health at regular time periods. I cannot receive TYSABRI® if I do not agree to follow the requirements of the TOUCH Prescribing Program
- I must notify the TOUCH Prescribing Program if I switch prescribers or infusion sites
- I have received, read, and understand the Patient Medication Guide
- I will bring to each TYSABRI® infusion a list of all medicines and treatments that I have taken during the last month Prescriber Acknowledgement I acknowledge that:

- I have read and understand the full Prescribing Information for TYSABRI®
- TYSABRI® is indicated as monotherapy for relapsing forms of MS
- This patient has a relapsing form of MS based on clinical and radiological evidence
- TYSABRI® increases the risk of progressive multifocal leukoencephalopathy (PML), an opportunistic viral infection of the brain that usually leads to death or severe disability. Although the cases of PML were limited to patients with recent or concomitant exposure to immunomodulators or immunosuppressants, there were too few cases to rule out the possibility that PML may occur with TYSABRI® monotherapy
- I am able to diagnose and manage opportunistic infections and PML, or am prepared to refer patients to specialists with these abilities
- Because TYSABRI® increases the risk of PML, it is generally recommended for patients who have had an inadequate response to, or are unable to tolerate, alternate MS therapies. I have discussed other MS treatments with this patient
- TYSABRI® is not ordinarily recommended for patients who are receiving chronic immunosuppressant or immunomodulatory therapy, or who are significantly immunocompromised from any other cause
- This patient has no known contraindications to TYSABRI® treatment, including PML
- I have instructed the patient to promptly report to me any continuously worsening symptoms that persist over several days
- This patient should be seen and evaluated 3 months after the first infusion, 6 months after the first infusion, at least every 6 months thereafter for as long as the patient receives TYSABRI®, and for at least 6 months after TYSABRI® has been discontinued
- I will determine every 6 months whether this patient should continue on TYSABRI® and if so, authorize treatment every 6 months
- I should report, as soon as possible, any case of PML, any hospitalization due to opportunistic infection, and any death to Biogen Idec
- Data concerning this patient and me will be entered into the mandatory TOUCH Prescribing Program. Biogen Idec requires my cooperation with periodic data collection. Failure to provide the requested information or otherwise comply with the requirements of the TOUCH Prescribing Program may result in discontinuation of TYSABRI® treatment for this patient and forfeiture of my authorization to prescribe TYSABRI®
- I have received educational materials regarding the benefits and risks of TYSABRI® treatment
- I have, or another healthcare provider under my direction has, educated this patient on the benefits and risks of treatment with TYSABRI®, provided him or her with the Patient Medication Guide and Enrollment Form, instructed him or her to read these materials, and encouraged him or her to ask questions when considering TYSABRI®

3.2 Enrollment Process for Prescribers and Patients

Biogen Idec will maintain the complete list of prescribers and patients authorized in the TOUCH Prescribing Program in the TOUCH database.

Figure 3:
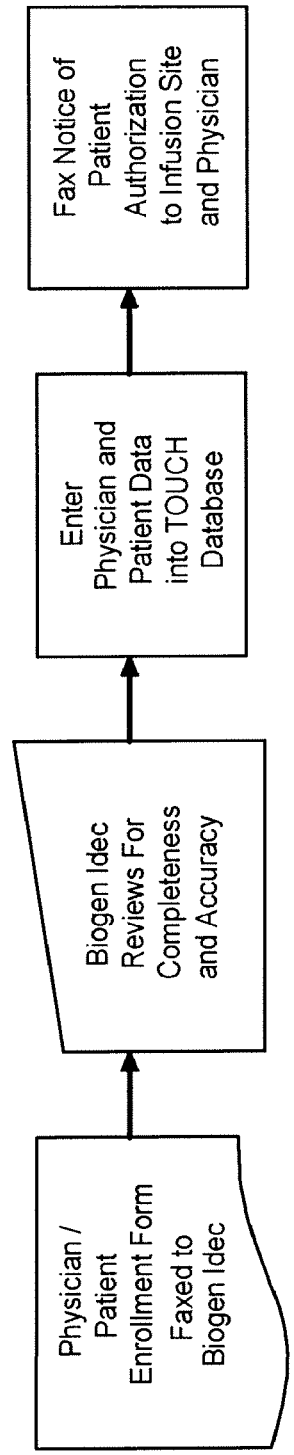
FIG. 3 is a schematic of an enrollment process for prescribers and patients.

As described in FIG. 3, Biogen Idec will review the submitted Prescriber/Patient Enrollment Form for completeness and accuracy, and verify that both the prescriber and the patient have signed the form. The prescriber and patient information will be entered into the TOUCH database. Biogen Idec will confirm the patient name, social security number (if provided) and date of birth against all current and previous patients in the database in order to avoid duplicate entries. At that time, a unique Patient Enrollment Number will be assigned to the patient in the TOUCH database, which should remain the same for that patient, even if the patient de-enrolls and subsequently re-enrolls into the program. Biogen Idec will assign a case manager to the patient. Then Biogen Idec will match the patient to an authorized infusion site, or confirm that the infusion site to which the prescriber has referred the patient is authorized in the TOUCH Prescribing Program.

Biogen Idec will communicate initial patient enrollment to both the infusion site and prescriber by means of a Notice of Patient Authorization fax. The infusion site will use this Notice of Patient Authorization to verify patient enrollment in the TOUCH Prescribing Program before administering the first dose of TYSABRI® to the patient. After the infusion site notifies Biogen Idec that the first dose has been administered (see Section 4.6), Biogen Idec will communicate current patient enrollment status to both the infusion site and the prescriber by means of a second Notice of Patient Authorization fax. The patient authorization period stated on this second fax is 6 months from the first confirmed infusion. Both the start and stop date of the authorization period are noted on the fax. If an infusion site misplaces the Notice of Patient Authorization fax, they may call Biogen Idec at 1-800-456-2255 and request a replacement Notice of Patient Authorization fax.

The prescriber must complete and sign a new Prescriber/Patient Enrollment Form for every patient of his or hers that enrolls into the TOUCH Prescribing Program. In addition, after a patient has authorized, the prescriber must reauthorize TYSABRI® use for that patient every 6 months, as described in Section 6.5.

3.3 Process for Patients who Change Prescribers

Patients attest on the Prescriber/Patient Enrollment Form that they will inform Biogen Idec when and if they change prescribers. The patient will be required to complete a new Prescriber/Patient Enrollment Form with the new prescriber to ensure that the new prescriber is authorized in the TOUCH Prescribing Program, and that the patient and new prescriber have discussed the known risks and potential benefits of TYSABRI® treatment. Biogen Idec will then inform the infusion site of the change in prescriber. If a patient does not inform Biogen Idec when he/she changes prescribers, Biogen Idec will obtain this information during the TYSABRI® Patient Status Report and Reauthorization Questionnaire process (see Section 6.3).

3.4 Process for Patients who Change Infusion Sites

Patients attest on the Prescriber/Patient Enrollment Form that they will inform Biogen Idec if they change infusion sites. If a patient changes infusion sites, Biogen Idec will verify that the new infusion site is authorized in the TOUCH Prescribing Program and then Biogen Idec will send a Notice of Patient Authorization fax with the patient's enrollment number and authorization period to the new infusion site and the prescriber. Biogen Idec will send Notice of Discontinuation to the previous infusion site stating that the patient is no longer eligible to receive treatment at that site. In the event that the patient changes infusion sites and does not inform Biogen Idec, Biogen Idec will identify this information when the new infusion site contacts Biogen Idec to obtain the Notice of Patient Authorization. Upon notice of the new infusion site, Biogen Idec will update the infusion site data linked to the patient in the TOUCH database and provide the new infusion site with the Notice of Patient Authorization Fax.

3.5 Process for Patients who are Hospitalized

If a patient is hospitalized and due for his or her next infusion, the patient may receive TYSABRI® at an authorized infusion site within the hospital if medically appropriate. The patient must be physically moved to the authorized infusion site to receive TYSABRI® under the care of the trained personnel who will administer the infusion. The authorized infusion site will contact Biogen Idec to obtain the Notice of Patient Authorization for that patient. If the hospital does not have an authorized infusion site, the infusion should be deferred until the patient is discharged and able to return to his or her usual authorized infusion site.

3.6 Prescriber De-Enrollment from the TOUCH Prescribing Program

By signing the Prescriber/Patient Enrollment Form, prescribers will acknowledge that a significant pattern of non-compliance with the requirements of the RiskMAP may result in his or her de-enrollment from the TOUCH Prescribing Program and forfeiture of authorization to prescribe TYSABRI®. Affected patients will be directed to other authorized prescribers in the area; if this is not possible, then the affected patients could potentially be de-authorized as well (see Section 10.3.2)

3.7 Patient Discontinuation from the TOUCH Prescribing Program

If a patient discontinues TYSABRI® treatment as indicated on the TYSABRI® Patient Status Report and Reauthorization Questionnaire (described in Section 6.4), or by notifying Biogen Idec, Biogen Idec will call the infusion site, communicate the patient's discontinuation, confirm the patient is not scheduled for future TYSABRI® infusions and send a Notice of Discontinuation to the prescriber, patient and infusion site stating that the patient is no longer authorized in the TOUCH Prescribing Program, and is not authorized to continue TYSABRI® treatment. Biogen Idec will document these calls to the infusion site.

If a prescriber indicates that a patient is lost to follow-up, Biogen Idec will attempt to contact that patient. If the patient plans to continue TYSABRI®-treatment, he/she will be instructed to contact his or her new prescriber to complete a new Prescriber/Patient Enrollment form. If this new Prescriber/Patient Enrollment form is not completed, Biogen Idec will communicate to the prescriber, patient and infusion site that the patient is no longer authorized in the TOUCH Prescribing Program, and is not authorized to continue TYSABRI® treatment. If Biogen Idec is unable to contact the patient, we will communicate to the prescriber and infusion site that the patient is no longer authorized to receive TYSABRI® treatment (see Section 10.3.2).

Prescribers will be required to complete a Patient Discontinuation Questionnaire when a patient discontinues TYSABRI® and 6 months after the patient discontinues TYSABRI®, as outlined in Section 6.8.

3.8 Re-Enrollment into the TOUCH Prescribing Program

A patient who is interested in re-starting TYSABRI® treatment is required to complete a new Prescriber/Patient Enrollment Form with his or her prescriber. Biogen Idec will follow the same enrollment processes to assist the patient in starting therapy. The patient will have the same unique Patient Enrollment Number as before, so that Biogen Idec can measure each patient's exposure to TYSABRI® over time. Therefore, the patient's new enrollment is linked to his or her prior enrollment, and Biogen Idec will be able to measure a patient's TYSABRI® exposure over time, or during a particular enrollment period.

4. Mandatory Training and Enrollment of Infusion Sites

TYSABRI® will be shipped only to and administered only at infusion sites authorized in the TOUCH Prescribing Program. Authorized infusion sites are sites that have been trained by Biogen Idec and Elan on the known risks, potential benefits and appropriate use of TYSABRI®, using educational materials. The infusion sites must also agree to comply with the RiskMAP requirements.

4.1 Criteria for Selection of Infusion Sites

Biogen Idec estimates that, after completion of the infusion site training, approximately 2,000 infusion sites will become authorized to administer TYSABRI®. An infusion site can be located in a hospital, a stand-alone clinic, or a physician's office. Infusion sites will be selected based on capability to execute the required RiskMAP activities, as well as patient need and geography. Biogen Idec and Elan will try to assure that each geographic region has an adequate number of authorized infusion sites to provide appropriate patients access to TYSABRI® therapy.

4.2 Training of Infusion Sites

Biogen Idec and Elan representatives will visit infusion sites, prior to their authorization, and provide training on the known risks, potential benefits, and appropriate use of TYSABRI® using the various TOUCH documents, including TOUCH Education Slide Set, Pre-infusion Patient Checklist, and Medication Guide. Infusion sites will be instructed that healthcare providers should promptly report serious adverse events to Biogen Idec. Infusion sites will be required to distribute the TYSABRI® Medication Guide and complete a Pre-infusion Patient Checklist for each patient prior to each monthly infusion and forward the Pre-infusion Patient Checklist including the date of infusion to Biogen Idec.

4.3 Infusion Site Enrollment Form

To enroll in the TOUCH Prescribing Program, the infusion site completes and signs the Infusion Site Enrollment Form. The infusion site will designate a person with appropriate authority to sign the Infusion Site Enrollment Form on behalf of the infusion site. The infusion site must acknowledge the following:

Infusion Site Acknowledgement
  A representative of Biogen Idec or Elan Pharmaceuticals, Inc. has provided training and education materials on the TOUCH Prescribing Program
  TYSABRI® will be administered only to patients who are enrolled in the TOUCH Prescribing Program
  Only currently authorized patients will receive TYSABRI®. Authorization is confirmed by ensuring that there is a current Notice of Patient Authorization on file and that the site has not received a Notice of Patient Discontinuation.
  Each patient will receive a copy of the TYSABRI® Patient Medication Guide prior to each infusion
  A TYSABRI® Pre-infusion Patient Checklist must be completed for every patient scheduled to receive TYSABRI®. The Pre-infusion Patient Checklist must be faxed to Biogen Idec within 1 business day of patient visit, and a copy placed in the patient's medical record
  I understand that, per the requirements of the TOUCH Prescribing Program, this infusion site may be audited by the Food and Drug Administration (FDA), Biogen Idec, Elan Pharmaceuticals, Inc., and/or a third party designated by the FDA, Biogen Idec, or Elan Pharmaceuticals, Inc.
  Noncompliance with the requirements of the TOUCH Prescribing Program will result in de-enrollment of the infusion site and forfeiture of the authorization to infuse TYSABRI®

After completing and signing the Infusion Site Enrollment Form, the infusion site faxes it to Biogen Idec.

4.4 Infusion Site Enrollment Process

Biogen Idec will maintain the complete list of authorized infusion sites in the TOUCH database.

As described in FIG. 4, when Biogen Idec receives the Infusion Site Enrollment Form, Biogen Idec will verify that the form is complete, accurate and signed. Then Biogen Idec will enter the infusion site information into the TOUCH database, thus initiating enrollment and authorization of the infusion site in the TOUCH Prescribing Program. At that time, a unique Site Authorization Number will be assigned to the infusion site in the TOUCH database and Biogen Idec will fax a Site Authorization Confirmation. The infusion site will be instructed to use the Site Authorization Number when ordering TYSABRI®. If an infusion site misplaces the Site Authorization Confirmation fax, the site may call Biogen Idec at 1-800-456-2255 to request a copy.

4.5 Pre-Infusion Patient Checklists

Prior to each infusion, an authorized infusion site must verify the patient is currently authorized to receive TYSABRI® treatment from the medical record. In order to do this, the site must refer to the patient's medical record and complete the following steps prior to every infusion.

1. If the patient did not receive his or her previous infusion, and physician clearance was required, the site must confirm authorization from the prescriber before providing the current infusion.
2. Confirm that there is a current Notice of Patient Authorization on file and verify the infusion is within the current authorization period.
3. Confirm there is not a Notice of Discontinuation on file. As stated previously in Section 3.7, if the patient discontinues TYSABRI®, Biogen Idec will call the infusion site, communicate discontinuation, confirm the patient is not scheduled for future TYSABRI® infusions and send a Notice of Discontinuation to the prescriber, patient and infusion site stating that the patient is no longer authorized in the TOUCH Prescribing Program, and is not authorized to continue TYSABRI® treatment. Biogen Idec will document these calls to the infusion site.

Only if the patient is authorized to receive TYSABRI®, the site next provides the patient with the TYSABRI® Medication Guide, gives the patient time to read the Medication Guide, and completes the Pre-Infusion Patient Checklist.

Infusion nurses will be instructed to complete the Pre-infusion Patient Checklist for each patient prior to each TYSABRI® infusion.

In order to assure that patient care is not jeopardized due to late communication of reauthorization, infusion sites will be allowed to provide one infusion past the authorization date. If a patient presents outside of the authorized period, the infusion site is required to call Biogen Idec. Biogen Idec will record all infusions that take place during this period.

The Pre-infusion Patient Checklist is designed to minimize inappropriate use of TYSABRI® and to facilitate early detection of worsening neurological symptoms that might be indicative of PML through regular, monthly assessments by infusion nurses at infusion sites. Using the Pre-Infusion Checklist, the infusion nurse is instructed to ask the following questions to the patient:

Pre-Infusion Patient Checklist Questions:

1. Over the past month, have you had any new or worsening medical problems (such as a new or sudden change in your thinking, eyesight, balance, strength, or other problems) that have persisted over several days?
2. Do you have a medical condition that can weaken your immune system, such as HIV infection or AIDS, leukemia or lymphoma, or an organ transplant, that may suggest that your body is not able to fight infections well?
3. In the past month, have you taken medicines to treat cancer or MS or any other medicines that weaken your immune system? (Review the list on the reverse side with the patient.)

4. In the past month, other than for the treatment of a recent relapse, have you taken any of the following medicines: Solu-Medrol®, methylprednisolone, Decadron®, dexamethasone, Depo-Medrol®, prednisone, or other steroid medicines?

If the patient answers NO to questions 1, 2, 3, and 4, the patient may be infused. If the patient answers YES (or the patient does not know the answer) to any of questions 1, 2, 3, or 4, then the patient should not be infused at that time, and the prescriber should be contacted for further instructions. After the infusion nurse discusses the findings with the patient's prescriber, the prescriber may give authorization to proceed with the infusion. Otherwise, the infusion must not be given and the patient must be promptly referred to their prescriber for further evaluation. The infusion nurse must document if authorization was given, and for all patients, the infusion nurse will document whether or not the patient was infused. The Pre-Infusion Patient Checklist must be faxed to Biogen Idec regardless of whether or not the patient received the infusion.

Thus, the Pre-Infusion Patient Checklist is designed to trigger a neurologist's consultation if the patient reports any worsening neurological symptoms lasting several days, if the patient reports any medical condition that may lead to an immunocompromised state (e.g., HIV infection), or if the patient reports receiving any concurrent immunomodulatory or immunosuppressant therapies, or steroid use.

4.6 Real-Time Centralized Collection and Tracking of Pre-Infusion Patient Checklists So that the Sponsor may monitor infusion site compliance with completion of the Pre-Infusion Patient Checklist and track infusions on a real-time, patient-specific basis, the infusion site must fax the Pre-Infusion Patient Checklist to Biogen Idec within 1 business day after the patient's infusion visit, whether the patient received the TYSABRI® infusion or not.

As described in FIG. 5, the Pre-Infusion Patient Checklist data will be entered into the TOUCH database whenever Biogen Idec receives a Pre-Infusion Patient Checklist. The Pre-Infusion Patient Checklist data will be linked to the patient, infusion site and prescriber data in the TOUCH database. A history of Pre-Infusion Patient Checklist data will be tracked for each patient, each infusion site and each prescriber.

In a later phase of the program, infusion sites may be able to use a web-based system to directly enter the Pre-Infusion Patient Checklist data into the TOUCH database, or continue to fax to Biogen Idec. This web-based system may simplify monitoring of compliance with the TOUCH Prescribing Program and tracking of individual patient dosing.

4.7 Diligence with Follow-Up of Missing Pre-Infusion Patient Checklists

Biogen Idec will make diligent efforts to obtain a completed Pre-Infusion Patient Checklist from every infusion site on every patient every month.

The Pre-Infusion Patient Checklist asks for the next scheduled infusion date, which will assist Biogen Idec in targeting when the next infusion will be given. If a date of next infusion is provided, Biogen Idec will follow-up on a missing Pre-Infusion Patient Checklist 3 days after that date.

If this next scheduled infusion date field is left blank, Biogen Idec will follow-up with the infusion site 45 days after the previous infusion, based on the following assumptions. The TYSABRI® approved PI will indicate that infusions are administered every 4 weeks. Assuming a 14-day window to allow for patient scheduling variation and an additional 3 days for variability surrounding the infusion site submission of the completed Pre-Infusion Patient Checklist, Biogen Idec expects to receive almost all completed Pre-Infusion Patient Checklists within 45 days after the previous infusion. If the Pre-Infusion Patient Checklist has not been submitted within this timeframe, Biogen Idec will telephone the infusion site in order to determine whether:

1. The patient has received a TYSABRI® infusion but the infusion site has not yet submitted the Pre-Infusion Patient Checklist, OR
2. The infusion appointment is scheduled to occur shortly, OR
3. The patient did not come to his or her scheduled infusion appointment In the case of (1), Biogen Idec will request that the infusion site send in the completed checklist and will remind the infusion site that a checklist must be completed on every patient before every dose and promptly submitted to Biogen Idec. Significant non-compliance on the part of the infusion site may result in de-enrollment of the infusion site and forfeiture of the authorization to administer TYSABRI® (see Section 10.3.2 for De-Enrollment Process).

In the case of (3), Biogen Idec will contact the prescriber to determine whether the patient is alive, whether the patient is receiving TYSABRI®, and whether the patient has developed PML or other serious OI. If attempts to obtain information from the prescriber are unsuccessful, then Biogen Idec will attempt to contact the patient directly in order to determine if the patient is alive, whether the patient is on TYSABRI® treatment, whether the patient has been hospitalized, and to remind the patient to contact his or her prescriber. If the patient has died, has PML, or other serious OI, or has been hospitalized, the Biogen Idec Drug Safety will diligently investigate the case and report to the FDA as appropriate.

If after these attempts, Biogen Idec is unable to reach the patient, then Biogen Idec will follow the Patient Discontinuation process outlined in Section 3.7. Significant non-compliance with these requirements on the part of the prescriber may result in de-enrollment of the prescriber and forfeiture of the authorization to prescribe TYSABRI®, after review by the TYSABRI® Compliance Review Committee (See Section 10.3.2). Affected patients will be directed to other authorized prescribers in the area; if this is not possible, then the affected patients could potentially be de-authorized as well. Similarly, a persistent pattern of non-compliance on the part of the infusion site may result in de-enrollment of the infusion site and forfeiture of the authorization to administer TYSABRI®, after review by the Compliance Review Committee (described in Section 10.1 and 10.3.2).

If the patient has discontinued TYSABRI®, Biogen Idec will follow the Patient Discontinuation process outlined in Section 3.7. Biogen Idec will then contact the prescriber 6 months later to complete a TYSABRI® Discontinuation Questionnaire to obtain the final safety follow-up on the patient (described in Section 6.8).

Consistent with the PI, the Sponsor recommends that TYSABRI® be administered every 4 weeks (28 days). TYSABRI® clinical trials permitted dosing within +/−5 days of the 28-day dosing interval.

4.8 Follow-Up of Pre-Infusion Patient Checklist Findings

Biogen Idec intends to follow-up on certain findings on the Pre-Infusion Patient Checklists. When Biogen Idec receives a completed Pre-Infusion Patient Checklist, Biogen Idec will review the data on the Checklist. Biogen Idec will call the infusion site to follow-up on incomplete or illegible forms. The Sponsor will follow-up within two business days to obtain this information.

If Biogen Idec receives a checklist in which the infusion site did not provide the Medication Guide, and/or confirm the patient's enrollment status, and the patient was infused, Biogen Idec will send a fax to the infusion site instructing the site of these requirements prior to every infusion. In addition, in other cases of infusion site non-compliance (e.g., the answer to Question 1, 2, 3, or 4 was YES, the patient was infused but the prescriber did not approve the infusion), Biogen Idec will contact the site to re-enforce its TOUCH Prescribing Program obligations with respect to the Pre-Infusion Patient Checklist.

As discussed during the Advisory Committee meeting, Biogen Idec expects that a high proportion of submitted Pre-Infusion Patient Checklists will contain reports of "worsening symptoms" that are in fact, MS-related symptoms, including relapses. The Pre-Infusion Patient Checklist is designed to trigger prescriber consultation in the event that the patient reports such symptoms and in turn, prescribers are required to report any case of PML to Biogen Idec promptly. Therefore, Biogen Idec will notify the prescriber in the event that the answer to Questions 1, 2, 3, or 4 is YES and the form indicates that the infusion site did not notify the prescriber. Under these circumstances, Biogen Idec will contact the prescriber and inform him/her of the findings and recommend further evaluation, if justified (see Section 10.2.5). In addition, the checklist prompts infusion personnel to refer to the previous checklist prior to an infusion. If the previous checklist notes that follow-up with the prescriber was required, infusion site personnel must confirm authorization from the prescriber was obtained prior to providing the current infusion.

Because PML is a rare event and because neurological symptoms are common in MS patients, it is likely that the Pre-Infusion Patient Checklist will have a low "signal to noise" ratio with respect to worsening neurological symptoms indicative of PML. In light of this, Biogen Idec is proposing an aggressive approach to follow-up on a single missing Pre-Infusion Patient Checklist, as a missing checklist may be more likely to be indicative of a prolonged dose suspension in the setting of PML or another serious adverse event (see Section 4.7).

5. Mandatory Enrollment of Central Pharmacies

Central pharmacies that dispense TYSABRI® to authorized infusion sites must also enroll in the TOUCH Prescribing Program. Note that central pharmacies are distinct from specialty pharmacies described in Section 2. Central pharmacies are located within a hospital, group practice, or infusion site, and are affiliated with an infusion site (i.e., the central pharmacy stores product inventory and releases it to an infusion site locally). Retail pharmacies and wholesalers are excluded from holding and dispensing TYSABRI®.

5.1 Central Pharmacy Enrollment Form

Biogen Idec or Elan will provide training to central pharmacies by providing the various TOUCH Prescribing Program educational materials, including the TOUCH Prescribing Program Slide Set and Inventory Log. The central pharmacy will designate a person with appropriate authority to sign the Central Pharmacy Enrollment Form on behalf of the central pharmacy. By signing the form, central pharmacies acknowledge the following:

Central Pharmacy Acknowledgement

The central pharmacy acknowledges that:

A representative of Biogen Idec or Elan Pharmaceuticals, Inc. has provided training and educational materials on the TOUCH Prescribing Program Central pharmacies may dispense TYSABRI® only to authorized infusion sites The TYSABRI® Inventory Tracking Log must be completed for every dose of TYSABRI® dispensed to authorized infusion sites. Inventory Tracking logs must be kept for at least 5 years from the date of the final log entry.

I understand that, per the requirements of the TOUCH Prescribing Program, this central pharmacy may be audited by the Food and Drug Administration (FDA), Biogen Idec, Elan Pharmaceuticals, Inc., and/or a third party designated by the FDA, Biogen Idec, or Elan Pharmaceuticals, Inc.

Noncompliance with the requirements of the TOUCH Prescribing Program may result in de-enrollment of the central pharmacy and forfeiture of the authorization to dispense TYSABRI®

The completed and signed form must be faxed to Biogen Idec.

5.2 Central Pharmacy Enrollment Process

Figure 6:
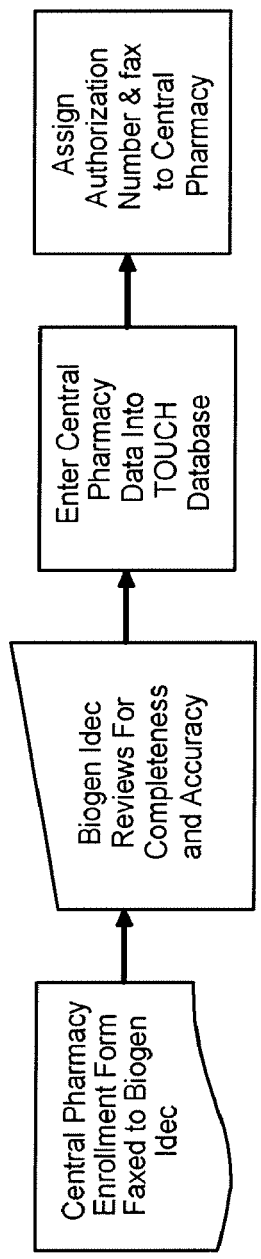
FIG. 6 is a schematic of a central pharmacy enrollment process.

Biogen Idec will maintain the complete list of authorized central pharmacies in the TOUCH database. As described in FIG. 6, these pharmacies will be entered into the TOUCH database when Biogen Idec receives a properly completed Central Pharmacy Enrollment Form. At that time, a unique Site Authorization Number will be assigned to the central pharmacy in the TOUCH database. Biogen Idec will fax the Central Pharmacy a Site Authorization Confirmation, which includes an Site Authorization Number, and a list of affiliated authorized infusion sites. This Site Authorization Number will be used by the central pharmacy to order TYSABRI®. If a Central Pharmacy misplaces the Site Authorization Confirmation, they may call Biogen Idec at 1-800-456-2255 and request a copy.

6. Systematic Tracking of All TYSABRI®-Treated Patients 6.1 TOUCH Prescribing Program Safety Surveillance Goals The TOUCH Prescribing Program is designed to assess the incidence and risk factors for PML and other serious OI with TYSABRI® treatment. In contrast to the typical post-marketing surveillance model that relies on spontaneous reporting of adverse events to the manufacturer, Biogen Idec through the TOUCH Prescribing Program, will systematically follow and actively solicit information regarding the occurrence of PML and other serious opportunistic infections through a variety of mechanisms on every TYSABRI®-treated patient in the US. The TOUCH Prescribing Program will seek to provide a complete denominator of TYSABRI®-treated patients (including person-years of exposure) and a complete numerator of any PML or other serious OI that may occur. In addition, careful analysis of any case of PML or other serious OI may provide insights into potential risk factors for such events.

Thus, Biogen Idec will closely monitor the incidence, rate, and morbidity and mortality of PML and other serious OI over time after the re-introduction of TYSABRI® into the US market. Any clinically significant change in the estimated risk of PML or other serious OI will trigger a prompt discussion with the FDA and appropriate action.

6.2 Multimodality Safety Tracking for PML and Other Serious OI

The TOUCH Prescribing Program is intended to provide diligent safety surveillance and systematic tracking of all patients treated with TYSABRI® for the occurrence of PML and other serious OI. Biogen Idec will actively solicit information regarding the occurrence of PML and other serious OI through multiple methodologies.

Through monthly, real-time collection of Pre-Infusion Patient Checklists, Biogen Idec will track TYSABRI® dosing on an up-to-date, individual patient basis. Biogen Idec has proposed an intensive diligence process to follow-up on missing Pre-infusion Patient Checklists or on Pre-Infusion Patient Checklists with findings (Section 4.7 and 4.8).

On the mandatory Prescriber/Patient Enrollment Form, prescribers must attest to report to Biogen Idec any case of PML, other serious OI, or death (Section 3.1).

On the mandatory Prescriber/Patient Enrollment Form, patients must attest that they will report to their prescriber any new or worsening symptoms that last several days, especially nervous symptoms (Section 3.1). The Medication Guide also provides these instructions to the patient. If the prescriber determines that the symptoms are related to PML then the prescriber is obligated to report the case to Biogen Idec.

The TOUCH Prescribing Program Overview will be disseminated to healthcare professionals involved in TYSABRI® treatment and will instruct them to report serious adverse events to Biogen Idec at 1-800-456-2255.

For additional diligence, Biogen Idec will actively query prescribers every 6 months on each of their patients regarding the occurrence of PML, other serious OI, or death using a TYSABRI® Patient Status Report and Reauthorization Questionnaire, described in Section 6.3. If a patient discontinues TYSABRI® treatment, Biogen Idec will actively follow-up on the status of such a patient as described in Section 3.7 and 6.8, respectively.

Thus, Biogen Idec has multiple mechanisms, in addition to spontaneous reporting, to help assure that if PML or other serious OI occurs, Biogen Idec will be informed about it as soon as possible.

6.3 Description of TYSABRI® Patient Status Report and Reauthorization Questionnaire The TYSABRI® Patient Status Report and Reauthorization Questionnaire will be sent to every prescriber for every patient every 6 months.

The purpose of this questionnaire is to ascertain the vital status of the patient and the occurrence of PML or other serious OI, and for the prescriber to reauthorize the patient to continue to receive TYSABRI® for the next 6 months. Specifically, prescribers will be asked whether the patient is still under their care, whether the patient is alive, whether the patient has a diagnosis of PML or has been hospitalized for an opportunistic infection. In addition, the Questionnaire will ask whether the patient is receiving or has received within the last 6 months any immunomodulatory or immunosuppressant therapies, whether the patient is currently or has received within the last 6 months any systemic steroids, whether the patient has received intermittent steroids within the last 6 months, and whether the prescriber is authorizing the continuation of TYSABRI® treatment in this patient for the next 6 months. Biogen Idec will fax the questionnaire to the prescriber who will be expected to complete and return it to Biogen Idec by fax or mail.

6.4 TYSABRI® Patient Status Report and Reauthorization Questionnaire Process

Figure 7:
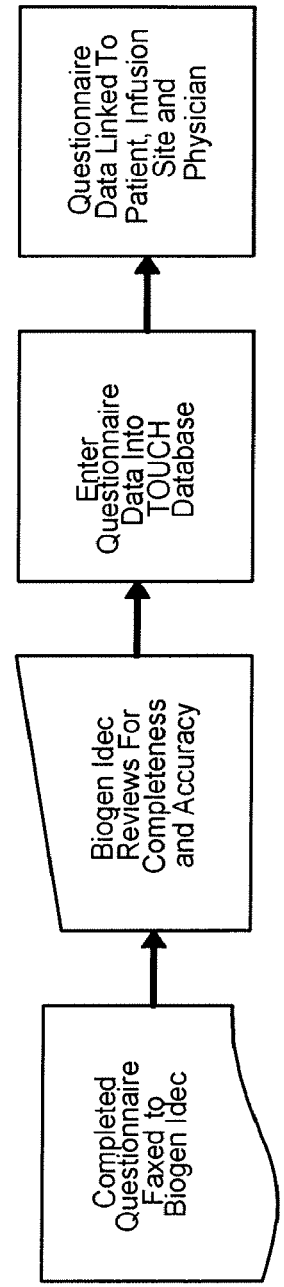
FIG. 7 is a schematic of a TYSABRI® Patient Status Report and Reauthorization Questionnaire data collection process.

Biogen Idec will maintain the data from each TYSABRI® Patient Status Report and Reauthorization Questionnaire in the TOUCH database. As described in FIG. 7, these data will be entered into the TOUCH database whenever Biogen Idec receives a TYSABRI® Patient Status Report and Reauthorization Questionnaire. Biogen Idec will verify that the data are complete and accurate. If there is missing information on the questionnaire, Biogen Idec will contact the prescriber to provide the missing information. If Biogen Idec does not receive the questionnaire in a timely fashion from the prescriber, Biogen Idec has a diligence process to obtain a completed questionnaire (described in Section 6.7). If a prescriber reports a case of PML, other serious OI, or death on the questionnaire, Biogen Idec Drug Safety will rapidly contact the prescriber and diligently obtain more information on the case (described in Section 7). Biogen Idec will report to FDA in an expedited basis (within 15 calendar days) all confirmed PML cases, as well as cases of serious OI or death (described in Section 10.2.1).

The TYSABRI® Patient Status Report and Reauthorization Questionnaire data will be linked to the patient, infusion site and prescriber data in the TOUCH database. A history of the TYSABRI® Patient Status Report and Reauthorization Questionnaire data will be tracked for each patient and each prescriber. In a later phase of the program, prescribers may have the option of using a web-based system to directly enter the Questionnaire data into the TOUCH database. This web-based capability may simplify monitoring of compliance with the TOUCH Prescribing Program.

6.5 Reauthorization Process for Every Patient Every 6 Months

The prescriber must reauthorize TYSABRI® use for the patient every 6 months using the TYSABRI® Patient Status Report and Reauthorization Questionnaire. Note that all data fields on the questionnaire must be completed and the answers appropriate (i.e., the prescriber has answered Questions A, B, C, and D as YES, YES, NO, and NO, respectively, as described in Section 6.6). In addition, the prescriber must authorize the continuation of TYSABRI® in order for the patient to continue to receive TYSABRI® treatment.

An appropriately completed questionnaire is a requirement for the patient to continue to receive TYSABRI® treatment. In order for the prescriber to be able to complete this questionnaire, the Sponsor expects that the prescriber will have recently examined the patient. By requiring reauthorization for TYSABRI® use through the use of this questionnaire, Biogen Idec helps to facilitate close clinical follow-up of the patient by their prescriber, including patient-prescriber visits every 6 months. Upon reauthorization, a Notice of Patient Authorization will be sent to the prescriber and infusion site with the new patient authorization period. Infusion site personnel will be prompted to confirm that the patient is currently authorized prior to every infusion via directions on the Pre-Infusion Patient Checklist.

If the prescriber does not reauthorize the continuation of TYSABRI® treatment, then Biogen Idec will follow the patient discontinuation process outlined in Section 3.7 Biogen Idec will then send the prescriber a final follow-up TYSABRI® Patient Discontinuation Questionnaire on this patient 6 months later, as described in Section 6.7.

6.6 Follow-Up of Findings on the TYSABRI® Patient Status Report and Reauthorization Questionnaires Question A: Is this patient still under your care?

If the answer to this question is NO and the prescriber does not know the name of the new prescriber caring for the patient, then Biogen Idec will contact the patient to determine whether the patient is still receiving TYSABRI® treatment and to obtain the name and contact information of the patient's new prescriber.

If the patient is still receiving TYSABRI® treatment but has changed prescribers, then Biogen Idec will remind the patient of his or her obligation to notify Biogen Idec upon changing prescribers, and will send a Prescriber/Patient Enrollment Form to the new prescriber to request completion and return to Biogen Idec. Then Biogen Idec will send the new prescriber a TYSABRI® Patient Status Report and Reauthorization Questionnaire to complete on this patient.

If the patient is no longer receiving TYSABRI® treatment, Biogen Idec will follow the Patient Discontinuation process outlined in Section 3.7. Biogen Idec will contact the patient's current prescriber 6 months later to complete a TYSABRI® Patient Discontinuation Questionnaire on this patient.

Question B: Is the patient alive?

If the answer is NO, Biogen Idec Drug Safety will rapidly contact the prescriber and will diligently obtain detailed information on the case. The follow-up of death is described in Section 7.

Question C and D: Does the patient have a diagnosis of PML that you have not already reported to Biogen Idec? Has the patient been hospitalized for an opportunistic infection that you have not already reported to Biogen Idec?

If the answer to either of these questions is YES or UNDER INVESTIGATION, Biogen Idec Drug Safety will rapidly contact the prescriber and will diligently obtain detailed information on the case. The follow-up of suspected PML and other serious OI is described in Section 7.

Question E: Is the patient currently or has the patient received intermittent courses of steroids for the treatment of MS relapse in the previous 6 months? If YES, please indicate the number of courses received.

These data can be used to characterize the pattern of intermittent use of steroids in the TOUCH prescribing program population.

Question F: Is the patient currently or has the patient received any immunomodulatory or immunosuppressant therapies in the previous 6 months? If YES, please indicate the type of therapy (AVONEX, Betaseron, Copaxone, Rebif, Novantrone, Azathioprine, Methotrexate, Mycophenolate, Cyclophosmamide, Chronic Systemic Steroids or Other immunomodulatory or immunosuppressive therapy) and number of months of use.

If the answer to this question is YES, Biogen Idec will send the prescribing physician a letter warning them that TYSABRI® is indicated for use as a monotherapy and warning against the use of TYSABRI® in combination with other immunosuppressants or immunomodulators.

Question G: If the patient is still under your care, do you authorize the continuation of TYSABRI® treatment for the next 6 months for this patient?

For the patient to continue to receive TYSABRI®, the answer to question G must be YES. (Of course, the patient must not have or be under investigation for PML or serious OI to continue TYSABRI® treatment).

If the Answer to G is NO, then Biogen Idec will follow the Patient Discontinuation process outlined in Section 3.7. Biogen Idec will then send the prescriber a TYSABRI® Patient Discontinuation Questionnaire 6 months later to ascertain the status of the patient.

6.7 Diligence with Follow-Up of Missing TYSABRI® Patient Status Report and Reauthorization Questionnaires Biogen Idec will make diligent efforts to obtain a completed TYSABRI® Patient Status Report and Reauthorization Questionnaire from the prescriber on each authorized patient every 6 months.

For every patient every 6 months, Biogen Idec will send the prescriber the questionnaire approximately 5 months after the first dose or 5 months after the most recent previous TYSABRI® Patient Status Report and Reauthorization Questionnaire (which ever is later). If there is no response, then Biogen Idec will send the prescriber a second copy of the questionnaire. If after these attempts the prescriber does not provide this information, Biogen Idec will contact the prescriber by telephone up to 3 times. If the prescriber has still not completed the questionnaire, then Biogen Idec will make up to 2 telephone contacts directly to the patient. The purpose of these patient contacts is to determine the vital status of the patient, whether the patient is on TYSABRI® treatment, whether the patient has been hospitalized, and remind the patient to contact their prescriber. If the patient has died or has been hospitalized, the Biogen Idec Drug Safety will rapidly and diligently investigate the case.

If Biogen Idec cannot reach the patient despite these attempts, Biogen Idec will follow the Patient Discontinuation process outlined in Section 3.7. A significant pattern of non-compliance with these requirements on the part of the prescriber may result in de-enrollment of the prescriber and forfeiture to prescribe TYSABRI®, upon review by the Compliance Review Committee. Affected patients will be directed to other authorized prescribers in the area (see Section 10.3.2).

If the patient has changed prescribers, then Biogen Idec will contact the new prescriber to request completion and submission of a new Prescriber/Patient Enrollment Form to Biogen Idec. Then, Biogen Idec will send the new prescriber a TYSABRI® Patient Status Report and Reauthorization Questionnaire to complete on the patient and send back to Biogen Idec.

6.8 TYSABRI® Patient Discontinuation Questionnaire: Follow-Up for Patients who Discontinue TYSABRI® Treatment Biogen Idec has designed several mechanisms to determine whether a patient may have discontinued TYSABRI® treatment. These include:

A prescriber may complete, and fax in a Patient Discontinuation Notification Form. This form will be provided to prescribers in the Enrollment Kit.

Through monthly collection of Pre-Infusion Patient Checklists, Biogen Idec will track TYSABRI® dosing on an individual patient basis. By diligently following-up on any missing Pre-infusion Patient Checklists, Biogen will identify any patient who has discontinued TYSABRI® treatment (Section 4.7 and 4.8).

Biogen Idec will identify patient discontinuations through the TYSABRI® Patient Status Report and Reauthorization Questionnaire (e.g., if the prescriber does not authorize the continuation of TYSABRI® dosing in the patient).

Biogen Idec may also confirm patient discontinuations through spontaneous reporting by the patient, prescriber, or infusion site.

If a patient discontinues TYSABRI® treatment, Biogen Idec will follow the Patient Discontinuation process outlined in Section 3.7. Physicians will be expected to complete a TYSABRI® Patient Discontinuation Questionnaire both at the time that the patient discontinues TYSABRI® as well as 6 months after their last dose. At both these timepoints, the prescriber will be sent a TYSABRI® Patient Discontinuation Questionnaire to complete and send back to Biogen Idec. This questionnaire queries the prescriber regarding the vital status of the patient, and the occurrence of PML or other serious OI.

The same diligence process described in Section 6.7 will be applied to facilitate the receipt of the completed TYSABRI® Patient Discontinuation Questionnaire. In addition, as described in Section 6.6, if there is a report of patient death, PML, or other serious OI on the questionnaire, then Biogen Idec Drug Safety will rapidly contact the prescriber and will diligently obtain detailed information on the case.

6.9 TOUCH Prescribing Program: Summary of Patient Data Collection

Figure 8:
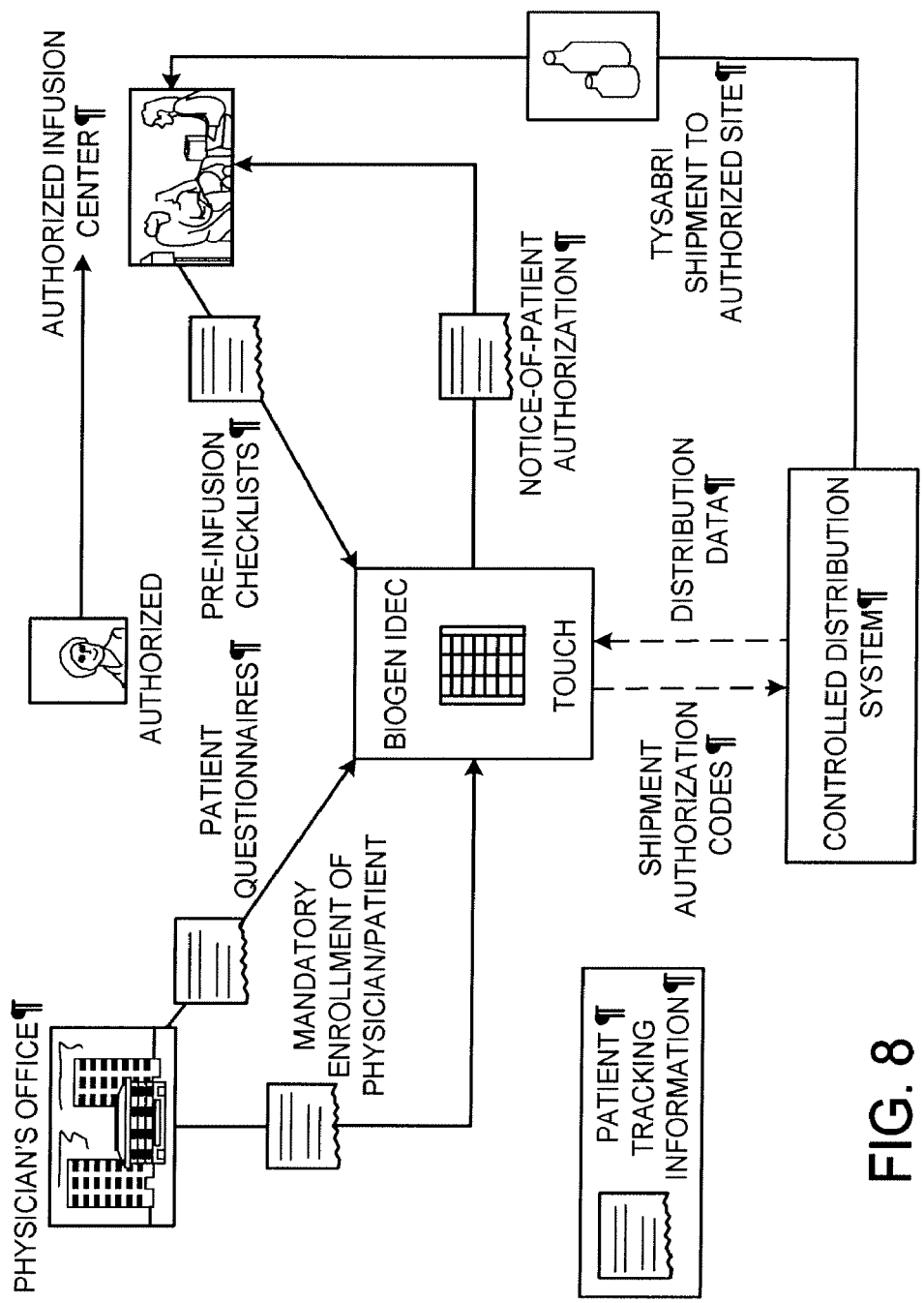
FIG. 8 is a schematic of data collection in TOUCH Prescribing Program.

At the heart of the TOUCH Prescribing Program is an integrated, computerized, validated database that captures enrollment, patient tracking, and drug distribution data, as presented in FIG. 8.

Biogen Idec will collect the following data in the TOUCH Prescribing Program:

Prescriber/Patient Enrollment Form

The Prescriber/Patient Enrollment Form will be used to collect the following data on each patient:
  patient's name, contact information, and social security number
  date of birth
  gender
  signed prescriber acknowledgement
  signed patient acknowledgement
  name of the most recent MS therapy
  duration of most recent MS therapy
  any prior TYSABRI® treatment
  infusion site information
  TYSABRI® prescription
  Monthly Pre-Infusion Patient Checklist The following data will be collected on each Pre-Infusion Patient Checklist:
  Dosing information, i.e., whether dose was administered, date of dosing
  Patient receipt of Medication Guide
  Patient report of worsening neurological symptoms lasting several days
  Patient report of new medical conditions that could compromise immune function
  Patient report of concomitant use of antineoplastic, immunosuppressant or immunomodulatory agents
  Patient report of concomitant steroid use
  Prescriber consultation in event of findings on checklist; documentation of authorization to infuse TYSABRI® was received
  Next scheduled infusion date (if known)
  TYSABRI® Patient Status Report and Reauthorization and Patient Discontinuation Questionnaires The following data will be collected on these questionnaires:
  Treating prescriber
  Vital Status
  Occurrence of PML
  Occurrence of hospitalization for an opportunistic infection
  Prescriber authorization to continue TYSABRI® (Patient Reauthorization Questionnaire only)
  Treatment with any concurrent immunomodulatory or immunosuppressant therapies or chronic systemic corticosteroids including number of months received (Patient Reauthorization Questionnaire only)
  Treatment with intermittent corticosteroids, including number of courses received (Patient Reauthorization Questionnaire only)
  TYSABRI® Distribution Data:
  Central Distributor information: unique identifier, name, invoice number, location shipped from
  SPP information: unique identifier, name, location shipped from
  Shipment information: quantity shipped, quantity returned, date
  Ship-to information: identifier, name, address, class of trade
  Shipment Authorization code: as obtained from TOUCH database for each shipment In addition to data above, Biogen Idec will collect the date of patient discontinuation from TYSABRI® treatment (see Section 6.8), as well as data collected through the course of diligence efforts (e.g., missing Pre-Infusion Patient Checklists, see Section 4.7). Note that diligence efforts in response to Pre-Infusion Patient Checklists will be coordinated with diligence efforts in response to Patient Status and Reauthorization and Discontinuation Questionnaires.

Finally, Biogen Idec will collect adverse events reported through the TOUCH Prescribing Program. These adverse events, whether reported by a patient, prescriber, or other person, will be entered and tracked in Biogen Idec's Drug Safety's Global Database (Oracle AERS). Reporting of pre-infusion patient checklist data will be handled consistently with section 10.2.5.

7. Special Assessments for PML, Other Serious OI, and Death

Biogen Idec Drug Safety will rapidly, diligently, and actively seek, and follow up on, all relevant details and source information of each case of PML, serious OI, or death, both those reported spontaneously and those reported through the Patient Status and Reauthorization and Discontinuation Questionnaires, to enable adequate assessment of the diagnosis, the course of the event, and potential predisposing factors. Biogen Idec Drug Safety will promptly contact the prescriber to request complete clinical details on each case, as well as submission of relevant source documentation (e.g., pathology results, microbiology results), potential predisposing factors (e.g., prior and concurrent therapies, underlying co-morbidities), clinical course and outcome.

Specifically, any report of PML will be evaluated in the following manner:
  Biogen Idec will rapidly attempt to contact the prescriber to obtain detailed information about the patient, using a PML-specific questionnaire. Biogen Idec will request full clinical details as well as submission of source documentation (such as clinical findings, MRI, and CSF JC viral DNA results).
  A case of PML will be considered confirmed based on pre-defined criteria that have been developed in collaboration with external independent experts. Specifically, a case will be considered confirmed by the presence of JC viral DNA in either the cerebrospinal fluid (CSF) or brain biopsy, in the appropriate clinical and MRI setting.
  If the diagnosis of PML is indeterminate, the Biogen Idec will submit the source documentation on the case to an external PML expert for an opinion of the diagnosis.
  Finally, a qualitative analysis of the case will be performed to identify any potential risk factors for PML development (e.g., prior or concomitant therapies, underlying co-morbidities, etc).

Similar diligence will be exercised in the investigation of any report of serious opportunistic infection or death of any cause. If a patient has died, the death certificate will be obtained on the patient. If the patient was hospitalized, the patient's hospital records will be requested. Finally, the National Death Index will be queried to ascertain the vital status of any patient lost to follow-up (see Section 10.2.6).

For the purpose of expedited reporting, a serious OI is defined as an infection due to an organism that generally does not cause disease, or causes only mild or self-limited disease, in people with normally functioning immune systems, but causes more significant disease in people with impaired immunity. These infections are frequently severe, prolonged or disseminated. Examples include esophageal candidiasis, systemic fungal infections, Pneumocystis carinii pneumonia, mycobacterial infections (including both pulmonary and extra-pulmonary tuberculosis), chronic intestinal cryptosporidiosis, and disseminated viral infections (such as disseminated herpes or cytomegalovirus infections).

For any adverse event of special interest such as PML, other serious OI, or death, Biogen Idec Drug Safety will obtain the patient's exposure to TYSABRI® from the TOUCH database. In addition, Biogen Idec Drug Safety will request that the reporter provide the patient's exposure history to TYSABRI® (if any) prior to the patient's enrollment into the TOUCH Prescribing Program, including any prior commercial or clinical trial exposure, the number of doses, and the approximate dates. If such a patient had been previously exposed to TYSABRI® in a clinical trial, Biogen Idec Drug Safety would obtain that patient's TYSABRI® exposure from the clinical trial database (assuming that the reporter is able to provide the patient's name, date of birth, and the name of the investigator who previously authorized that patient into a TYSABRI® clinical trial or the location of the investigational site). Thus, Biogen Idec will attempt to ascertain the patient's total exposure to TYSABRI®, both within the TOUCH Prescribing Program and any previous exposure in clinical trials or commercially. This will facilitate analysis of the relationship, if any, between adverse events of interest and duration of TYSABRI® exposure. These adverse events will be entered and tracked in Biogen Idec Drug Safety's Global Safety Database (Oracle AERS).

Although occurrence of PML would be considered an "expected" event based on 21 C.F.R. 600.80 and the proposed revised Package Insert, Biogen Idec will nevertheless report all cases with a confirmed diagnosis of PML to the FDA on an expedited basis, i.e., within 15 calendar days of receipt of the case. In addition, other serious OI or death of any cause will be reported to the FDA on an expedited basis.

More details on the proposed reporting plan for PML, other serious OI, and death are provided in Section 10.2.1.

8. Risk Minimization Tools 8.1 Tools for Prescribers, Patients, Infusion Sites, and Central Pharmacies Biogen Idec sought feedback from neurologists, infusion sites, infusion nurses, central pharmacies and MS patients to develop materials that would be useful, effective, and practical for managing the risk of PML. Based upon this feedback, Biogen Idec has developed a number of tools that will educate healthcare providers, and thus their patients, about the potential risk for, and consequences of, PML with TYSABRI® treatment. Biogen Idec will use these materials, all subject to FDA review and approval, in educating healthcare providers, and thus patients, of the known risks and potential benefits of TYSABRI® treatment. These tools will be distributed directly to the infusion sites and prescribers with subsequent dissemination to patients. Patients and healthcare providers can also access up-to-date information at Biogen Idec's website, TYSABRI.com, and through a toll-free phone-line to Biogen Idec's call center. Distribution of enrollment forms will be controlled and available only from Biogen Idec and Elan directly. Materials that are essential to implementation of the risk management plan are listed in Table 2.

TABLE 2

| Material | Brief Description |
| --- | --- |
| Patient Medication Guide | The Medication Guide describes the known risks of TYSABRI ® in patient-oriented language. The Medication Guide will accompany the package insert. In addition, the Medication Guide will be shipped directly to infusion sites and provided prior to every infusion to every patient. |
| Large-Font Versions of Patient Medication Guide and Full Prescribing Information | Large-font version of FDA-approved labeling, to facilitate readability and functionality of this information. |
| TOUCH Prescribing Program Education Slide set | PowerPoint presentation to provide education necessary to execute TOUCH Prescribing Program |
| TYSABRI ® and TOUCH Prescribing Program Slide set | PowerPoint presentation that includes clinical data and an overview of the TOUCH Prescribing Program elements, intended for physicians and patients (2 sections) |
| TOUCH Prescribing Program Overview | General description of the TYSABRI ® risk management program outlining responsibilities for prescribers, infusion sites, central pharmacies, and patients. |
| Prescriber/Patient Enrollment Form | Form to be signed by all patients and prescribers for enrollment into the TOUCH Prescribing Program. |
| Infusion Site Enrollment Form | Form to be signed by infusion sites for enrollment into the TOUCH Prescribing Program and to obtain designation as an authorized infusion site. Only authorized infusion sites are eligible to receive TYSABRI ® shipments. |

TABLE 2-continued

RiskMAP Materials

| Material | Brief Description |
| --- | --- |
| Central Pharmacy Enrollment Form | Form to be signed by central pharmacies for enrollment into the TOUCH Prescribing Program and to obtain designation as an authorized central pharmacy. Only authorized central pharmacies are eligible to receive TYSABRI ® shipments and may dispense TYSABRI ® only to authorized infusion sites within their organization/institution. |
| TYSABRI ® Inventory Tracking Log | Tracking log required for use by central pharmacies to document dispensing of TYSABRI ® to authorized infusion sites associated to a central pharmacy |
| Pre-infusion Patient Checklist | Pre-infusion Patient Checklist to be used prior to each infusion for every patient on TYSABRI ®. Checklist must be submitted to Biogen Idec upon completion. |
| Patient Status Report and Reauthorization Questionnaire | Form that must be filled out every 6 months to obtain patient status and enable prescriber reauthorization of the patient in the TOUCH Program |
| Patient Discontinuation Notification Form | A form that may be used by prescribers to discontinue a patient and de-enroll them from the TOUCH Prescribing Program. |
| Patient Discontinuation Questionnaire | This form will be provided to prescribers when a patient discontinues TYSABRI ® treatment and 6 months after discontinuation. |
| TOUCH Enrollment Kit | A folder provided to potential prescribers that contains approved TOUCH Materials (listed above) and outlines specific responsibilities of each of the parties involved in the TOUCH Prescribing Program. |
| Dear Doctor Letter | Communication to neurologists containing important safety information regarding reintroduction of TYSABRI ® |
| Dear Patient Letter | Communication to patients who have expressed an interest in receiving updates regarding TYSABRI ®, containing important safety information regarding reintroduction of TYSABRI ® |
| Patient Getting Started Brochure | Brochure designed to assist patients considering starting treatment with TYSABRI ®. Contains summary information on the known risks and potential benefits of therapy, in addition to an overview of TOUCH Requirements. |
| Healthcare Professional Infusion Guide | Designed for use in the infusion-setting. Provides practical step-by-step considerations for appropriate infusion of TYSABRI ® and reinforcement of TOUCH requirements. |
| TYSABRI.com | Website designed to disseminate approved labeling information for TYSABRI ® and an overview of TOUCH Program requirements. |
| Guidance for Evaluation of New Neurologic Symptoms in Patients Receiving TYSABRI ® (natalizumab) | Document provides guidance to healthcare professionals when undertaking the assessment and management of new or worsening neurologic symptoms in multiple sclerosis (MS) patients treated with TYSABRI ®. |
| Additional Education | Biogen Idec will support various other initiatives to provide educational materials about the PML risk and appropriate-use conditions for TYSABRI ®, to neurologists and infusion nurses for use with MS patients. All neurologists in Biogen Idec's database, including prescribers who have completed and submitted a Prescriber/Patient Enrollment Form, will receive periodic educational mailings. Prescribers will be expected to share this information with their patients. These documents will be pre-cleared with DDMAC. A toll-free help-line will provide prescribers and nurses access to health care professionals in Biogen Idec's medical information department who can answer questions related to TYSABRI ®. Biogen Idec will support educational initiatives through the National MS Society (NMSS) Infusion Nurse Society (INS), International Organization for MS Nurses (IOMSN) and will facilitate the generation and dissemination of medical information on PML and TYSABRI ® through media such as review articles, seminars, and Continuing Medical Education (CME) programs directed at neurologists and infusion nurses. |

9. Additional Studies 9.1 TYSABRI® Global Observational Program in Safety (TYGRIS)

Biogen Idec proposes that a large subset of patients in the TOUCH Prescribing Program also enroll into a voluntary observational study called the TYSABRI® Global Observational Program in Safety (TYGRIS).

TYGRIS will enroll approximately 5,000 patients worldwide, of which approximately 3,000 patients will be authorized in the US, and these patients will be systematically followed for up to 5 years. Note that in the US, only prescribers and patients already authorized in the mandatory TOUCH Prescribing Program will be eligible to participate in the voluntary TYGRIS study. The objectives of this observational study are to determine the incidence and pattern of serious infections and malignancies, as well as the overall safety profile of TYSABRI® in MS patients with long-term use in clinical practice.

Whereas the TOUCH Prescribing Program is focused on determining the incidence of PML and other serious OI, TYGRIS will evaluate newly emerging risks, if any, with TYSABRI® monotherapy treatment in MS patients. While the safety profile of TYSABRI® in clinical trials has been well-characterized regarding the incidence and nature of common serious adverse events over a 2-year period, the incidence of rare events, the safety profile beyond 2 years, and the safety profile in clinical practice will be better characterized in this study. For example, while the clinical trial data on malignancy is reassuring, it would be important to evaluate the incidence of malignancy over the longer term because malignancies can be long-latency events. In addition to the very targeted data collection in the TOUCH Prescribing Program, data collection in an observational study such as TYGRIS allows Biogen Idec to evaluate a broader range of as yet unknown issues as well unexpected safety findings with TYSABRI® use in the clinical practice setting.

Baseline demographic data have been collected on all patients on the Prescriber/Patient Enrollment Form for the TOUCH Prescribing Program, as described in Section 6.9. For patients also participating in TYGRIS, additional baseline demographics will be collected, including past medical history (including history of serious infections, malignancies, other serious adverse events, and pregnancy status, if applicable), MS history (including past or current treatments), prior use and duration of immunomodulatory, antineoplastic, or immunosuppressive agents, and prior detailed use of TYSABRI®.

Thereafter, prescribers participating in TYGRIS are instructed to report any serious adverse event to Biogen Idec within 24 hours of the site becoming aware of the event. Participating prescribers will also be contacted every 6 months and will be asked to provide any serious adverse events that they have not yet reported as well as the patients' exposure to any concomitant antineoplastic, immunomodulatory or immunosuppressant therapies, or systemic corticosteroids. The RiskMAP discourages concurrent use of TYSABRI® with such therapies; therefore Biogen Idec anticipates that there should be little or no use of such therapies concurrently with TYSABRI®. It should also be noted that participating prescribers in TYGRIS in the US, like all prescribers authorized in the TOUCH Prescribing Program, must also reauthorize TYSABRI® dosing on every patient every 6 months.

Biogen Idec intends to recruit a large number of prescribers (approximately 250 in the US) from both private and hospital-based practices. Prescribers who will employ a central Institutional Review Board (IRB) for the study will be given preference for participation. In this way, Biogen Idec will strive to enroll into TYGRIS a patient population that is representative of patients treated in a clinical practice setting.

A sample size of 5000 MS patients will be enrolled and followed for 5 years whether continuing on TYSABRI® or not. Assuming a 20% discontinuation rate from TYSABRI® at the beginning of year 2 and a 10% annual discontinuation rate from TYSABRI® thereafter, it is estimated that 18,700 patient-years of TYSABRI® exposure will be completed in this study. Assuming approximately 1000 patient-years lost to follow-up, a total of 24,000 patient-years of follow-up will accrue. This study design will allow the detection of important rare serious adverse reactions that occur with an incidence of 0.06% with a 95% probability and an incidence of 0.05% with 92% probability.

9.2 Pregnancy Registry

Biogen Idec will establish a Pregnancy Registry in the US to determine the safety of TYSABRI® in pregnant patients. Approximately 300 TYSABRI®-exposed pregnant MS patients will be authorized. The primary objective of this study will be to evaluate any pattern or increase in birth defects in children of women with multiple sclerosis who were exposed to TYSABRI® at any time within 3 months prior to conception, or at any time during pregnancy, where the outcome of the pregnancy is unknown at the time of enrollment. The secondary objectives will be to descriptively evaluate the following outcomes in pregnant women exposed to natalizumab: live born infants, fetal loss (stillbirths, elective/spontaneous abortions), and gestational age, body weight, gender, head circumference, and length of child. Biogen Idec committed to this study as part of the post-approval commitments for the initial BLA.

9.3 Safety of Re-Exposure to TYSABRI®

In order to evaluate the safety of TYSABRI® with re-exposure after an interval without treatment, Biogen Idec will conduct two multi-national, open-label studies. Approximately 1,500 patients with MS who previously received TYSABRI® treatment during their participation in clinical studies will be authorized.

9.4 Effect of TYSABRI® on Immune Function

Biogen Idec will conduct a study in approximately 40 MS patients to evaluate the effect of TYSABRI® on humoral and cellular immunity to recall and neo-antigens. Both cellular (ex vivo proliferation responses) and humoral (specific serum immunoglobulin) immune responses to recall vaccine antigens (e.g., tetanus and pneumovax) and naïve antigens (KLH) will be studied with or without natalizumab treatment. Data from this study may provide information into potential immunological risk factors for PML with TYSABRI® treatment. Biogen Idec committed to this study as part of the post-approval commitments to the initial BLA.

9.5 Non-Clinical Studies

A direct animal model of JC virus associated PML has not been described. Biogen Idec will initiate specific in vitro studies to investigate the effects of natalizumab interaction with specific cellular targets and functions with respect to JC virus infection and replication. In addition, the effects of short-term alpha 4-integrin inhibition in rodent and guinea pig experimental autoimmune encephalomyelitis will be evaluated, specifically with respect to effects on immune function. These non-clinical studies, while exploratory, may provide insights into potential immunological risk factors for PML with TYSABRI® therapy.

10. Evaluation/Quality Plan

Biogen Idec and Elan are committed to evaluating the effectiveness of the TYSABRI® RiskMAP and reporting the results on a quarterly basis to the FDA. Each submission will include two major datasets: (1) Health Outcomes Data (e.g., PML rate, overall safety), and (2) Systems/Process Data, Quality and Compliance Metrics. The specific type and frequency of data that the Sponsor will submit to the FDA is outlined in detail in this Section. A more detailed description of the systems and compliance data being monitored and evaluated can be found in the Quality Plan.

A key feature of the Sponsor's RiskMAP evaluation process will be internal senior management review of these data by a multi-disciplinary TYSABRI® Risk Management Review Committee.

The Evaluation/Quality Plan will allow Biogen Idec to assess the effectiveness of the RiskMAP in an ongoing fashion and to improve the plan, as necessary.

10.1 TYSABRI® Risk Management Review Committee

A multi-disciplinary TYSABRI® Risk Management Review Committee composed of senior representatives from Biogen Idec and Elan's Drug Safety, Clinical, Commercial, Regulatory, Legal, and Quality Departments will be formed. This Committee will evaluate the effectiveness of the risk management plan on a quarterly basis, both from a health outcomes perspective (e.g., PML rate, overall safety) as well from a systems/process perspective (e.g., Quality Plan execution and systems/compliance metrics). This Committee will also make decisions regarding any major corrective actions to the RiskMAP, if needed. The decisions and outcomes of this Committee will be included in the quarterly reports to the FDA.

10.1.1 TYSABRI® Safety Review Committee

Biogen Idec and Elan will create a joint TYSABRI® Safety Review Committee chaired by Drug Safety and Risk Management of Biogen Idec and composed of a cross-functional team from both Biogen Idec and Elan. The Purpose of this Committee is to review TYSABRI® safety data and to determine appropriate corrective actions, if needed. The Committee will meet on a regular basis to review the data discussed in Section 10.2 of this document.

10.1.2 TYSABRI® Compliance Review Committee

Biogen Idec and Elan will create a joint TYSABRI® Compliance Review Committee chaired by Quality at Biogen Idec and composed of a cross-functional team from both Biogen Idec and Elan. The Purpose of this Committee is to facilitate RiskMAP compliance and effective execution of the Quality Plan. The Committee will meet on a monthly basis, and as needed, to review results from monitoring of operational processes, distribution data, audit data and any emerging trends or out of tolerance levels. In addition, this committee will determine the appropriate corrective action to be taken to address non-compliance and to ensure continuous improvement for any of the RiskMAP activities.

10.2 Health Outcomes Evaluation

The following results will be provided to the FDA, according to Table 3.

TABLE 3

Health Outcomes Evaluation: Metrics and Methods.

| Metric | Evaluation method | Expected date after re-introduction into US market |
|---|---|---|
| Baseline Demographics in TOUCH Prescribing Program (i.e., summary statistics on age, gender, relapsing MS diagnosis, most recent MS therapy, any prior TYSABRI ® exposure) | TOUCH Prescribing Program: Enrollment Form | Quarterly for the first year, biannually (every 6 months) for 2 years, then annually thereafter |
| Proportion of patients who have received concurrent immunomodulatory or immunosuppressant agents or chronic systemic corticosteroids and months of exposure to such therapies** Proportion of patients who have received intermittent corticosteroids and number of courses received | TOUCH Prescribing Program: Patient Status and Reauthorization Form | Quarterly for the first year, biannually (every 6 months) for 2 years, then annually thereafter |
| Baseline Demographics in TYGRIS (i.e., summary statistics as above, as well as past MS history, all prior immunomodulatory and immunosuppressant therapies, past medical history, past serious infections/malignancies/other SAEs) | TYGRIS Study | Quarterly for the first year, biannually (every 6 months) for 2 years, then annually thereafter |
| Proportion of patients concurrently treated with immunomodulatory or immunosuppressant agents** | TYGRIS Study | Quarterly for the first year, biannually (every 6 months) for 2 years, then annually thereafter |
| Listings and case narratives for all confirmed and suspected PML cases, other serious OI, and deaths; Estimate of PML and other serious OI incidence and rate (based on number of confirmed cases per 1000 persons/person-years of exposure); qualitative analysis of risk factors for PML and other serious OI based on review of confirmed cases | TOUCH Prescribing Program | Quarterly for the first year, biannually (every 6 months) for 2 years, then annually thereafter |

TABLE 3-continued

Health Outcomes Evaluation: Metrics and Methods.

| Metric | Evaluation method | Expected date after re-introduction into US market |
|---|---|---|
| Listing, incidence, and rate of patients who discontinued TYSABRI ® | TOUCH Prescribing Program | Quarterly for the first year, biannually (every 6 months) for 2 years, then annually thereafter |
| Post-Marketing Safety | Adverse Events collected from the TOUCH Prescribing Program | PSUR* every 3 months for first 2 years, then semi-annually |
| Incidence and pattern of serious infections and malignancies | TYGRIS Study | Yearly Interim Clinical Study Reports Note that related SAEs from TYGRIS will be provided in the PSUR*. |
| Results of National Death Index Search | National Death Index | Every 12 months |
| Safety with Re-Treatment | IND Annual Report for Re-Dosing Studies | Annually (final Clinical Study Report when studies completed) Note that related SAEs from these studies will be provided in the PSUR*. |
| TYSABRI ® impact on immune function | IND Annual Report for Immune Function/Vaccine Study | Annually (as well as final Clinical Study Report when studies completed) Note that related SAEs from these studies will be provided in the PSUR*. |
| TYSABRI ® impact on pregnancy outcomes | Pregnancy Registry | Analyses will be provided in the PSUR*. |

*PSUR = Periodic Safety Update Report, please see Section 10.2.4
**Consistent with the PI, TYSABRI ® is not ordinarily recommended in patients who are receiving chronic immunosuppressant or immunomodulatory therapy; therefore Biogen Idec anticipates little or no reported use of TYSABRI ® under these circumstances in the TOUCH Prescribing Program.

10.2.1 Expedited Reporting of Events of Interest (e.g., PML, Serious OI, Death) in the TOUCH Prescribing Program Following the commercial re-introduction of TYSABRI® into the US market, the Sponsor is proposing the following paradigm for the reporting of adverse events in the TOUCH Prescribing Program.

All spontaneous and solicited adverse event reports from any post-marketing source will be reported as per 21 CFR 600.80 (Post-marketing Reporting of Adverse Experiences).

In addition, the following describes the process for expedited reporting for key safety events from any source in the post-marketing space:

Progressive Multifocal Leukoencephalopathy:

The Sponsor will diligently follow-up on any report of possible PML, and will expedite to FDA within 15 calendar days any PML case considered confirmed by the presence of JC viral DNA in the CSF or brain biopsy in the appropriate clinical and Mill setting. All other possible cases, not confirmed by the presence of JC viral DNA in the CSF or brain biopsy, will be reported quarterly in the Periodic Report (Section 10.2.4).

Other Serious Opportunistic Infections and Deaths of Any Cause:

The Sponsor will diligently follow-up on and provide expedited reporting to FDA within 15 calendar days of receiving any report of other serious opportunistic infections or deaths of any cause. The definition for serious OI is provided in Section 7.

10.2.2 Expedited Reporting of Events of Interest from TYSABRI® Studies and Clinical Trials The Sponsor is proposing the following paradigm for the reporting of adverse events in TYSABRI® studies and clinical trials (i.e., TYGRIS and Re-Dosing Studies).

In TYSABRI® studies and clinical trials, all serious unexpected and related events will be reported in an expedited fashion to the Agency as per 21 CFR 312.32 (IND Safety Reports).

In addition, the following describes the process for expedited reporting for key safety events from any TYSABRI® studies or clinical trials:

Progressive Multifocal Leukoencephalopathy:

The Sponsor will diligently follow-up on any report of possible PML, and will expedite to FDA within 15 calendar days any PML case considered confirmed by the presence of JC viral DNA in the CSF or brain biopsy in the appropriate clinical and MRI setting, regardless of the investigator causality assessment.

Other Serious Opportunistic Infections:

The Sponsor will diligently follow-up on and expedite to FDA within 15 calendar days of receiving any report of other serious opportunistic infections, regardless of the investigator causality assessment. The definition for serious OI is provided in Section 7.

Deaths of Any Cause:

The Sponsor will diligently follow-up on any report of death and expedite to FDA within 15 calendar days any report of death that is unexpected and considered related according to the investigator. However, if the death is due to a confirmed case of PML or a serious OI, then the Sponsor will expedite within 15 calendar days regardless of the investigator causality assessment.

10.2.3 PML and Other Serious OI Incidence, Rate and Risk Factors

Biogen Idec will closely monitor the incidence, rate, and morbidity and mortality of PML and other serious OI over time after the re-introduction of TYSABRI® into the US market. Any clinically significant change in the risk of PML or other serious OI will trigger a prompt discussion with the FDA and appropriate action.

In addition, cases of confirmed PML and other serious OI will be tabulated every 3 months after re-introduction and provided to the FDA expressed as:

Number of cases per estimate of total population exposed (cases/persons exposed)

Number of cases per estimate of person-years of TYSABRI® exposure (cases/person-years exposure)

A qualitative analysis of any confirmed cases of PML and other serious OI will be made to identify any potential risk factors (e.g., prior or concomitant therapies, underlying co-morbidities, etc).

The person-years of exposure will be derived from the total number of patients treated with TYSABRI® in the TOUCH Prescribing Program and from the total number of TYSABRI® infusion administered (the latter will be obtained from the submitted Pre-Infusion Patient Checklist data).

10.2.4 Periodic Reports

Biogen Idec and Elan are proposing to substitute the Periodic Adverse Event Report (PAER) (as per 21 CFR 600.80 (c)(2)), with the international Periodic Safety Update Report (PSUR) (as per the International Conference on Harmonisation (ICH) guideline designated as ICH-E2C and published in the Federal Register on 19 May 1997).

This PSUR will be submitted quarterly for the first 2 years after re-introduction of TYSABRI®, and semi-annually thereafter.

10.2.5 Reporting of Pre-Infusion Patient Checklist Data

Biogen Idec will collect Pre-Infusion Patient Checklists to monitor infusion site compliance with this important requirement and to track the dosing of TYSABRI® on an individual patient basis. As discussed at the Advisory Committee meeting, Biogen Idec expects that these checklists, collectively, will contain an extremely high prevalence of reports of "worsening symptoms" that are, in fact, MS symptoms, including relapses. The Pre-Infusion Checklist is designed to trigger further follow-up (i.e., neurological consultation) under theses circumstances, and prescribers are required to report any cases of PML to Biogen Idec. Thus, Biogen Idec does not intend to report all cases of "continuously worsening symptoms" received in monthly Pre-Infusion Patient Checklists as adverse drug experiences under 21 C.F.R. 600.80. Instead, Biogen Idec will report all confirmed cases of PML, as well as serious opportunistic infections and deaths on an expedited basis.

10.2.6 Results of National Death Index Search

The National Death Index will be queried to ascertain the vital status of any patient lost to follow-up. The National Death Index provides a match with identifiers for a person who has died, the State of death, and the death certificate number. Then Biogen Idec will request the death certificates from the State Health Department. Recognizing that there is a lag time of approximately 18 months between patient death and the updating of records in the National Death Index, the results of these queries will be provided to the FDA every 12 months after commercial re-introduction.

10.3 Systems/Process, Quality and Compliance Metrics

The following results will be provided to the FDA, according to Table 4.

TABLE 4

Systems and Processes: Metrics and Methods

| Metric | Evaluation method | Expected Date |
|---|---|---|
| Prescriber knowledge and behavior regarding TYSABRI ® and PML | Prescriber survey | Every 6 months |
| Infusion nurse knowledge and behavior regarding TYSABRI ® and PML | Infusion nurse survey | Every 6 months |
| Availability and use of tools at infusion sites and prescriber offices | Prescriber survey and infusion nurse survey | Every 6 months |
| Percentage of vials shipped to authorized infusion sites and central pharmacies | Distribution data | Quarterly for the first year, biannually (every 6 months) for 2 years, then annually thereafter |
| Number of authorized patients, prescribers, infusion sites, central pharmacies | Enrollment Forms | Quarterly for the first year, biannually (every 6 months) for 2 years, then annually thereafter |
| Number of infusions administered | Pre-Infusion Patient Checklists and Phone calls to Infusions Sites | Quarterly for the first year, biannually (every 6 months) for 2 years, then annually thereafter |
| Percent and Number of Pre-Infusion Checklists received by Biogen Idec based on Confirmed Infusions | Pre-Infusion Patient Checklists | Quarterly for the first year, biannually (every 6 months) for 2 years, then annually thereafter |

TABLE 4-continued

Systems and Processes: Metrics and Methods

| Metric | Evaluation method | Expected Date |
| --- | --- | --- |
| Number of Checklists with a "No" response to Questions 1-4, number where infusion withheld, number where infusion was administered, number where prescriber was contacted, number where prescriber was unable to be contacted | Pre-Infusion Patient Checklists | Quarterly for the first year, biannually (every 6 months) for 2 years, then annually thereafter |
| Percent and Number of TYSABRI® Patient Status and Re-Authorization Questionnaire completed compared to questionnaires sent | TYSABRI® Patient Status Report and Reauthorization Questionnaire data | Quarterly for the first year, biannually (every 6 months) for 2 years, then annually thereafter |
| Number of TYSABRI® patients dosed outside of the re-authorization period | TYSABRI® Patient Status Report and Questionnaire data, and Pre-Infusion Checklists | Annually |
| Infusion Site compliance with submission of completed Pre-infusion Patient Checklists | Pre-infusion Patient Checklists | Quarterly for the first year, biannually (every 6 months) for 2 years, then annually thereafter |

The utility and ongoing need for the TOUCH Prescribing Program will be assessed 3 years after the re-introduction of TYSABRI®.

10.3.1 Audit Plan

Biogen Idec and Elan plan a detailed surveillance and audit process to monitor TOUCH Prescribing Program compliance and the control and dispensing of the drug. The ongoing monitoring will include verification of the completed Pre-Infusion Patient Checklists against data from the TOUCH Prescribing Program, verification of all distribution data to ensure that TYSABRI® is only shipped to authorized infusion sites and central pharmacies, that patients are affiliated to authorized infusion sites, and that pre-infusion checklists are collected from infusion sites and in alignment with distribution data. In addition to ongoing monitoring and reconciliation, Biogen Idec's Quality group will conduct audits at a select number of central pharmacies and infusion sites. Sites will be selected for audit based on a random sampling, taking into account geographic region and infusion center type. The auditors will perform a physical inventory and review accountability of product at the site. The auditors will also review certain TOUCH Prescribing Program related documentation. The auditors will report on noted discrepancies, such as, discrepancies in inventory levels or in TOUCH Prescribing Program forms. Significant noncompliance will be included in established exception reports and reviewed by the TYSABRI® Compliance Review Committee.

Routine compliance audits will be conducted at the single distributor and specialty pharmacies. As warranted, for cause audits will be conducted at a given site authorized in the TOUCH Prescribing Program.

Additional details of the monitoring and surveillance of the TOUCH program is contained in the Quality Plan.

10.3.2 De-Enrollment Process for Prescribers, Patients, Infusion Sites, Central Pharmacies, and Central Pharmacies for Non-Compliance The Compliance Review Committee will review drug distribution, Pre-Infusion Patient Checklist, and TYSABRI® Patient Status Report and Reauthorization Questionnaire compliance data to ensure all parties are compliant. The committee will review exceptions, monthly and on a case by case basis, and will make determinations as to whether any parties should be de-authorized in the TOUCH Prescribing Program due to significant non-compliance.

The system to handle non-compliance will be modeled after the Biogen Idec exception system used in the manufacturing, testing and distribution of product. Quality approved procedures will address identification, notification, investigation, impact assessment, corrective and preventive action, escalation, tracking, monitoring, trending and documentation for exceptions. An exception will be classified as major or minor based upon potential for significant impact on the objectives of the TOUCH Prescribing Program. An exception classified as minor is not likely to impact the objectives of the RiskMAP, however, recurring minor exceptions may be classified as major and may be indicative of a system issue. The Compliance Review Committee will promptly review major exceptions. Quality will reside over the Committee and have oversight in determination of corrective and preventive actions taken to address the root cause of non-compliance. In addition, exceptions will be reviewed monthly by the Compliance Review Committee, and quarterly by the TYSABRI® Management Review Committee, to assess suitability and effectiveness of procedures, processes and systems to meet the objectives of the RiskMAP.

10.3.2.1 Prescriber De-Enrollment Process for Non-Compliance

Significant non-compliance with the requirements of the TOUCH Prescribing Program may result in de-enrollment of the prescriber and forfeiture of the authorization to prescribe TYSABRI®. The Compliance Review Committee will consider such cases on a case-by-case basis. Affected patients will be directed to other authorized prescribers in the area; if this is not possible, then the affected patients could potentially be de-authorized as well.

10.3.2.2 Patient De-Enrollment Process for Non-Compliance

If a patient discontinues TYSABRI® as indicated on the TYSABRI® Patient Status Report and Reauthorization Questionnaire, or by notifying Biogen Idec, Biogen Idec will follow the Patient Discontinuation process outlined in Section 3.7. If a prescriber indicates that a patient is lost to follow-up, Biogen Idec will contact that patient. If the patient plans to continue TYSABRI®-treatment, he/she will be instructed to contact his or her new prescriber to complete a new Prescriber/Patient Enrollment form. If the form is not completed or Biogen Idec is unable to reach the patient, Biogen Idec will follow the Patient Discontinuation process outlined in Section 3.7.

10.3.2.3 Infusion Site Process for Non-Compliance

An authorized infusion site will be informed that significant non-compliance with the requirements of the TOUCH Prescribing Program may result in de-enrollment of the infusion site and forfeiture of its authorization to administer TYSABRI®. Actionable non-compliance may include actions such as dosing a non-authorized TYSABRI® patient, and non-compliance with the requirement to complete and submit the Pre-infusion Patient Checklist. The Compliance Review Committee will consider such cases on a case-by-case basis. In such cases, Biogen Idec will provide patients and prescribers with information about other authorized infusion sites in the area. Biogen Idec will notify central pharmacies not to distributed TYSABRI® to de-authorized infused sites.

10.3.2.4 Central Pharmacies Process for Non-Compliance

Significant noncompliance with the requirements of the TOUCH Prescribing Program may result in de-enrollment of the central pharmacy and forfeiture of the authorization to dispense TYSABRI®. Actionable non-compliance may include dispensing TYSABRI® to non-authorized infusion sites. The Compliance Review Committee will consider such cases on a case-by-case basis. Biogen Idec will notify infusion sites affiliated with central pharmacies about the central pharmacy de-enrollment.

10.3.2.5 Specialty Pharmacies

Specialty Pharmacies are contractually obligated to comply with the controlled distribution system requirements. Noncompliance with the RiskMAP requirements may result in de-enrollment of the Specialty Pharmacy and forfeiture of the authorization to dispense TYSABRI®. Actionable non-compliance may include dispensing TYSABRI® to non-authorized infusion sites or not providing distribution data. The Compliance Review Committee will consider such cases on a case-by-case basis.

10.3.3 Assessment of Knowledge and Behaviors

Knowledge, attitude and behavior (KAB) surveys will be developed to survey, prescribers and infusion site nurses on their knowledge of the key risk management messages of the TYSABRI® Risk Management Program and the actions taken to minimize risk. The surveys will be developed and tested prior to implementation using standard psychometric methods for survey research (e.g., health literacy, content validity). A more detailed description of the surveys will be provided to the FDA after approval.

10.3.3.1 Prescriber Survey

A sample of prescribers identified from the group of prescribers who have authorized into the TOUCH prescribing program will be invited to participate in the prescriber survey. For generalizability of results, a randomly selected statistical sample of prescribers will be used. Prescriber samples will be mailed a KAB survey and asked to return it in a postage paid envelope. If the survey is not returned within 2 weeks, a follow-up reminder post card will be mailed. Prescribers who do not respond within another two weeks will be telephoned and surveyed by direct interview. Each selected sample will be unique, i.e., prescribers will be interviewed only once in any given one year period.

10.3.3.2 Infusion Nurse Survey

A randomly selected, statistical sample of infusion nurses from the list of authorized infusion sites will be selected for the infusion nurse survey. An attempt will be made to include nurses who administer the Pre-Infusion Patient Checklist and infuse TYSABRI®. The selected infusion nurse will be mailed a KAB survey and asked to return it in a postage paid envelope. If the survey is not returned within 2 weeks, a follow-up reminder post card will be mailed. Infusion site nurses who do not respond within another two weeks will be telephoned and surveyed by direct interview.

Example 2

Exemplary Computer Implementation

Figure 9:
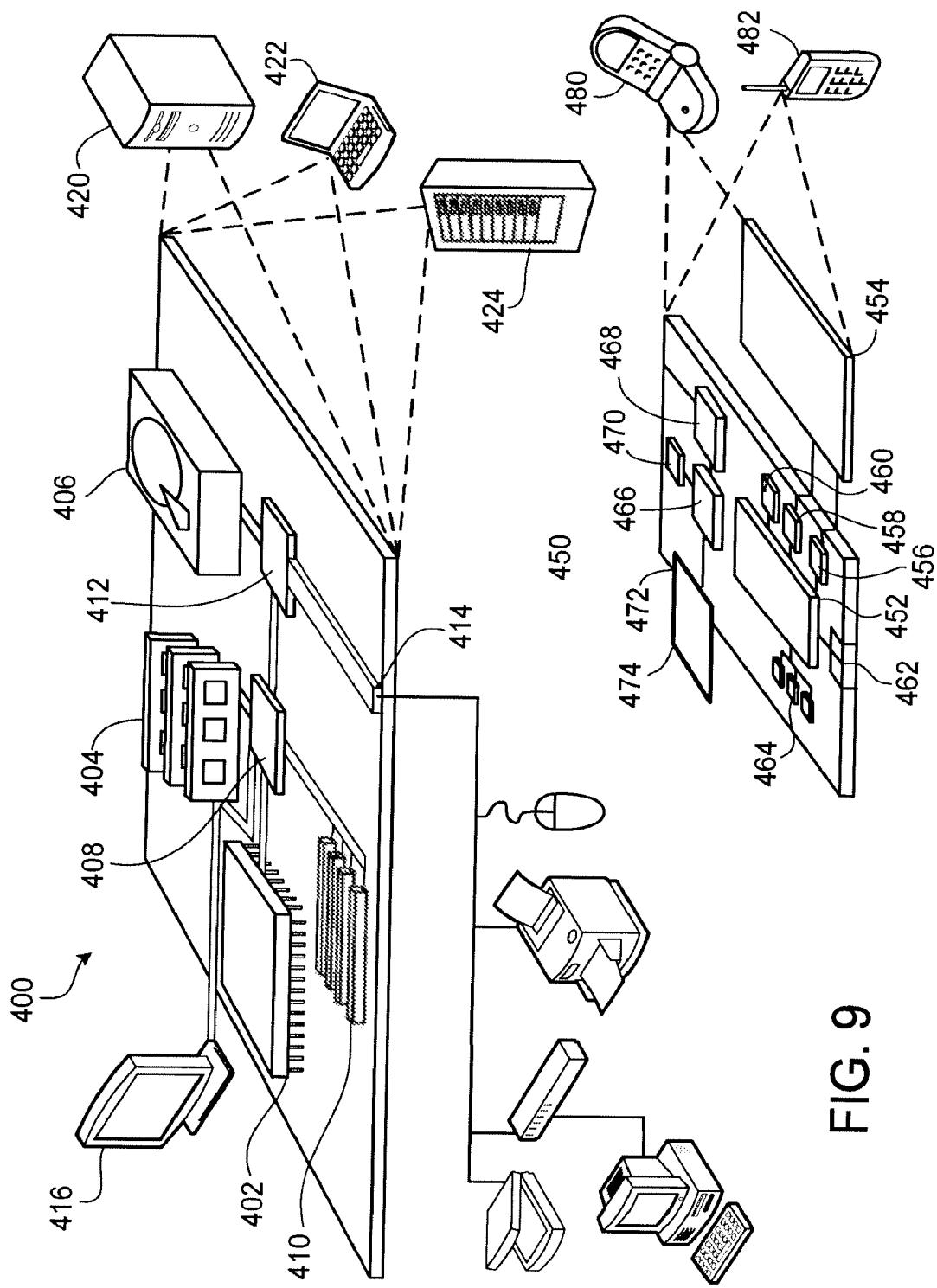
FIG. 9 is a block diagram of computing devices and systems.

In an exemplary computer implementation, FIG. 9 is a block diagram of computing devices and systems 400, 450. Computing device 400 is intended to represent various forms of digital computers, such as laptops, desktops, workstations, personal digital assistants, servers, blade servers, mainframes, and other appropriate computers. Computing device 450 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 400 includes a processor 402, memory 404, a storage device 406, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and can be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses can be used, as appropriate, along with multiple memories and types of memory. Also, multiple computing devices 400 can be connected, with each device providing portions of the necessary operations (e.g., as a server bank, a group of blade servers, or a multi-processor system).

The memory 404 stores information within the computing device 400. In one implementation, the memory 404 is a computer-readable medium. In one implementation, the memory 404 is a volatile memory unit or units. In another implementation, the memory 404 is a non-volatile memory unit or units.

The storage device 406 is capable of providing mass storage for the computing device 400. In one implementation, the storage device 406 is a computer-readable medium. In various different implementations, the storage device 406 can be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 404, the storage device 406, memory on processor 402, or a propagated signal.

The high speed controller 408 manages bandwidth-intensive operations for the computing device 400, while the low speed controller 412 manages lower bandwidth-intensive operations. Such allocation of duties is exemplary only. In one implementation, the high-speed controller 408 is coupled to memory 404, display 416 (e.g., through a graphics processor or accelerator), and to high-speed expansion ports 410, which can accept various expansion cards (not shown). In the implementation, low-speed controller 412 is coupled to storage device 406 and low-speed expansion port 414. The low-speed expansion port, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 400 can be implemented in a number of different forms, as shown in the figure. For example, it can be implemented as a standard server 420, or multiple times in a group of such servers. It can also be implemented as part of a rack server system 424. In addition, it can be implemented in a personal computer such as a laptop computer 422. Alternatively, components from computing device 400 can be combined with other components in a mobile device (not shown), such as device 450. Each of such devices can contain one or more of computing device 400, 450, and an entire system can be made up of multiple computing devices 400, 450 communicating with each other.

Computing device 450 includes a processor 452, memory 464, one or more input/output device such as a display 454, a communication interface 466, and a transceiver 468, among other components. The device 450 can also be provided with a storage device, such as a microdrive or other device, to provide additional storage. Each of the components 450, 452, 464, 454, 466, and 468, are interconnected using various buses, and several of the components can be mounted on a common motherboard or in other manners as appropriate.

The processor 452 can process instructions for execution within the computing device 450, including instructions stored in the memory 464. The processor can also include separate analog and digital processors. The processor can provide, for example, for coordination of the other components of the device 450, such as control of user interfaces, applications run by device 450, and wireless communication by device 450.

Processor 452 can communicate with a user(s) through one or more control interface 458 and display interface 456 coupled to a display 454. The display 454 can be, for example, a TFT LCD display or an OLED display, or other appropriate display technology. The display interface 456 can comprise appropriate circuitry for driving the display 454 to present graphical and other information to a user. The control interface 458 can receive commands from a user and convert them for submission to the processor 452. In addition, an external interface 462 can be provide in communication with processor 452, so as to enable near area communication of device 450 with other devices. External interface 462 can provide, for example, for wired communication (e.g., via a docking procedure) or for wireless communication (e.g., via Bluetooth or other such technologies).

The memory 464 stores information within the computing device 450. In one implementation, the memory 464 is a computer-readable medium. In one implementation, the memory 464 is a volatile memory unit or units. In another implementation, the memory 464 is a non-volatile memory unit or units. Expansion memory 474 can also be provided and connected to device 450 through expansion interface 472, which can include, for example, a SIMM card interface. Such expansion memory 474 can provide extra storage space for device 450, or can also store applications or other information for device 450. Specifically, expansion memory 474 can include instructions to carry out or supplement the processes described above, and can include secure information also. Thus, for example, expansion memory 474 can be provide as a security module for device 450, and can be programmed with instructions that permit secure use of device 450. In addition, secure applications can be provided via the SIMM cards, along with additional information, such as placing identifying information on the SIMM card in a non-hackable manner.

The memory can include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, memory on processor 452, or a propagated signal.

Device 450 can communicate wirelessly through communication interface 466, which can include digital signal processing circuitry where necessary. Communication interface 466 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 468. In addition, short-range communication can occur, such as using a Bluetooth, WiFi, or other such transceiver (not shown). In addition, GPS receiver module 470 can provide additional wireless data to device 450, which can be used as appropriate by applications running on device 450.

Device 450 can also communication audibly using audio codec 460, which can receive spoken information from a user and convert it to usable digital information. Audio codex 460 can likewise generate audible sound for a user, such as through a speaker, e.g., in a handset of device 450. Such sound can include sound from voice telephone calls, can include recorded sound (e.g., voice messages, music files, etc.) and can also include sound generated by applications operating on device 450.

The computing device 450 can be implemented in a number of different forms, as shown in the figure. For example, it can be implemented as a cellular telephone 480. It can also be implemented as part of a smartphone 482, personal digital assistant, or other similar mobile device.

Where appropriate, the systems and the functional operations described in this specification can be implemented in digital electronic circuitry, or in computer software, firmware, or hardware, including the structural means disclosed in this specification and structural equivalents thereof, or in combinations of them. The techniques can be implemented as one or more computer program products, i.e., one or more computer programs tangibly embodied in an information carrier, e.g., in a machine readable storage device or in a propagated signal, for execution by, or to control the operation of, data processing apparatus, e.g., a programmable processor, a computer, or multiple computers. A computer program (also known as a program, software, software application, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification can be performed by one or more programmable processors executing one or more computer programs to perform the described functions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, aspects of the described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The techniques can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

Example 3

Forms

TOUCH PRESCRIBING PROGRAM
TYSABRI outreach: Unified commitment to health

Inventory Tracking Log

Your Pharmacy Name: _____ Your Pharmacy Authorization Number: _____

For each vial of TYSABRI dispensed, you must use this Log to record*:
- Date dispensed
- Number of TYSABRI vials dispensed
- Name of clinic/infusion site to which TYSABRI is being dispensed
- Site Authorization Number for the infusion site to which TYSABRI is being dispensed. (If you do not have the Site Authorization Number on file and cannot obtain it from Biogen Idec at 1-800-456-2255, do not dispense TYSABRI)
- Your name (name of dispenser)

| Clinic/Infusion Site Name | Site Authorization Number |
|---|---|
|  |  |
|  |  |
|  |  |
|  |  |

- Biogen Idec will contact you if one of your associated infusion site's authorization is revoked. TYSABRI cannot be dispensed to unauthorized infusion sites
- If you have an associated infusion site that is not authorized and want it to become authorized, please contact Biogen Idec at 1-800-456-2255 (8:30 AM to 8:00 PM ET)
- Keep this log for at least 5 years from the date of the final log entry

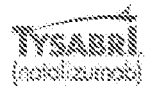
TYSABRI (natalizumab)

*Please note that per the requirements of the TOUCH Prescribing Program, this log may be audited by the Food and Drug Administration (FDA), Biogen Idec, Elan Pharmaceuticals, Inc., and/or a third party designated by the FDA, Biogen Idec, or Elan Pharmaceuticals, Inc.

What is claimed is:

1. A computer-implemented method of treating a plurality of patients having multiple sclerosis (MS) with natalizumab, wherein each patient is authorized to receive treatment with natalizumab responsive to an indication that the patient has not had progressive multifocal leukoencephalopathy (PML) and/or responsive to an indication that the patient does not have a contraindicated medical condition and/or responsive to an indication that the patient has not taken a contraindicated medication and has not received a contraindicated treatment, the method comprising, at a treatment site at which administration of natalizumab to treat the patient is authorized, administering natalizumab to treat each patient having a current authorization generated by a distributed system for tracking administration of natalizumab to each of the plurality of patients, the distributed system comprising a centralized administration system including a centralized computer and a database of patients, prescribers and treatment sites relating to the administration of natalizumab, and, at each authorized treatment site, the centralized administration system further comprising a computer system adapted to process the authorized patient, generation of the current authorization comprising, for each of the plurality of patients, prescribers and treatment sites relating to the administration of the natalizumab:

(i) the centralized computer storing, within the database, an indication that a treatment site is an authorized treatment site;

(ii) the centralized computer storing, within the database, an indication identifying whether one or more healthcare providers at an authorized treatment site has been trained on known risks, potential benefits, and appropriate use of natalizumab;

(iii) the centralized computer creating, within the database, a patient record for each patient that receives treatment with natalizumab;

(iv) the centralized computer creating, within the database, a prescriber record, the prescriber record indicating that a prescriber consents to provide, to an identified patient, natalizumab;

(v) the centralized administration system enrolling, each of the plurality of patients, responsive to storing patient and prescriber record information by the centralized administration system, wherein the patient record information indicates the patient's consent to receive treatment with the anti-VLA-4 antibody, and wherein the prescriber record information indicates the prescriber's consent to provide the patient with natalizumab;

(vi) the centralized administration system generating an indication, within the database, of an authorization of the patient as an authorized patient for treatment with natalizumab, responsive to the central administration system confirming that each of the patient record information and the prescriber record information is complete with respect to the patient's consent and the prescriber's consent;

(vii) responsive to a confirmation, the centralized administration system generating an authorization form and a unique patient identifier for the authorized patient in the database of the centralized administration system, wherein the authorization form is valid for a maximum of six months;

(viii) the computer system confirming enrollment of the authorized patient identified by the unique patient identifier in the centralized administration system;

(ix) confirm, by the computer system responsive to communication with the centralized administration system, the computer system confirming authorization of the authorized patient for treatment with natalizumab;

(x) the computer system completing complete, on the computer system, a treatment site checklist;

(xi) responsive to completion of the treatment site checklist, the centralized administration system providing an indication of authorization to administer natalizumab intravenously to the authorized patient by the one or more healthcare providers at the authorized treatment site;

(xii) treating the authorized patient by administering natalizumab at the authorized treatment site; and (xiii) the distributed system tracking administration of the natalizumab to at least 1,000 patients as each patient is treated at one of the plurality of treatment sites.

2. The computer-implemented method according to claim 1, further comprising the centralized administration system reauthorizing each authorized patient as a reauthorized patient by the central administrator for treatment with natalizumab, responsive to a collection, by the central administration system, of a patient status report and reauthorization questionnaire completed by the prescriber and a collection of information confirming that the patient to be reauthorized has not had PML or died, or received a contraindicated treatment within the last six months and that the prescriber reauthorizes treatment for the next six months, upon the collection of information confirming that the patient to be reauthorized has not had PML or died, or received a contraindicated treatment within the last six months and that the prescriber reauthorizes treatment for the next six months, and the centralized administration system generating a reauthorization form for the reauthorized patient, wherein the reauthorization form is valid for a maximum of six months; and the computer system:

processing the reauthorized patient at an authorized treatment site;

confirming enrollment of the reauthorized patient identified by the unique patient identifier in the centralized administration system;

responsive to communication with the centralized administration system, confirming authorization of the reauthorized patient for treatment with natalizumab;

completing a treatment site checklist; and responsive to completion of the treatment site checklist, providing an indication of authorization to administer natalizumab intravenously to the reauthorized patient by the one or more healthcare providers at the authorized treatment site.

3. The computer-implemented method of claim 1, further comprising treating relapsing forms of MS.

4. The computer-implemented method of claim 1 or 2, wherein the patient record information includes information that indicates that the patient to be authorized or reauthorized attests that he/she will report to his/her prescriber any new or worsening symptoms.

5. The computer-implemented method of claim 4, wherein the patient to be authorized or reauthorized attests that he/she will report to his/her prescriber new or worsening symptoms lasting several days.

6. The computer-implemented method of claim 4, wherein the new or worsening symptoms are nervous system symptoms.

7. The computer-implemented method of claim 1 or 2, wherein the patient record information includes information that indicates that the patient to be authorized or reauthorized attests to one or more of:
  (i) the patient to be authorized or reauthorized understands that natalizumab is approved for a specific condition;
  (ii) that the patient to be authorized or reauthorized has read a document that provides preselected information on natalizumab;
  (iii) that the patient to be authorized or reauthorized is aware that natalizumab is associated with a preselected risk which results in an undesirable outcome;
  (iv) that the patient to be authorized or reauthorized has discussed the risks and benefits of natalizumab with his/her physician;
  (v) that the patient to be authorized or reauthorized understands that he/she should call his/her physician promptly to report any continuously worsening symptoms;
  (vi) that the patient to be authorized or reauthorized understands that in order to receive natalizumab, he/she will automatically be enrolled in a registry;
  (vii) that the patient to be authorized or reauthorized understands that the patient information provided to the prescriber may be provided to the authorized treatment site;
  (viii) that the patient to be authorized or reauthorized understands that if he/she does not complete or sign a patient review form, he/she will not be able to receive natalizumab; and
  (ix) that the patient to be authorized or reauthorized agrees to bring to each treatment a list of all medications he/she has taken during the last month.

8. The computer-implemented method of claim 1 or 2, wherein the prescriber record information includes information that indicates that the prescriber attests that he/she will report any case of PML or death in the patient treated with natalizumab.

9. The computer-implemented method of claim 1 or 2, wherein the prescriber record information includes information that indicates that, for each patient for whom the prescriber may prescribe natalizumab, the prescriber attests to one or more of:
  (i) that the prescriber will provide the patient with information about natalizumab, will require the patient to read it and will discuss the known risks and potential benefits of natalizumab with the patient;
  (ii) that the prescriber has read the full prescribing information for natalizumab;
  (iii) that the prescriber is aware that natalizumab increases the risk of PML;
  (iv) that the prescriber understands that natalizumab is indicated for a preselected purpose;
  (v) that the prescriber will promptly report any case of PML to the centralized administration system;
  (vi) that the prescriber has discussed the risks and benefits of natalizumab and has discussed other therapies, with the patient;
  (vii) that the prescriber has confirmed that the patient has a relapsing form of MS, using preselected criteria;
  (viii) that the prescriber confirms that the patient has no known contraindications to natalizumab;
  (ix) that the prescriber is not prescribing any antineoplastic, immunosuppressant, or immunotherapies other than short courses of corticosteroids concurrently with natalizumab;
  (x) that the prescriber has instructed the patient to promptly report to his/her prescriber any continuously worsening symptoms that persist over several days;
  (xi) that the prescriber agrees to provide any information relating to the patient that may be necessary to assess the incidence of risk factors for PML and other adverse effects that may be associated with the treatment;
  (xii) that the prescriber is able to diagnose and manage the PML, or is prepared to refer patients to specialists with these abilities;
  (xiii) that the prescriber agrees that this patient should be seen and evaluated at a preselected time after the first administration, periodically thereafter for as long as the patient receives the drug, and for at least a preselected number of months after the drug has been discontinued;
  (xiv) that the prescriber will determine at a preselected interval whether this patient should continue on natalizumab and, if so, authorize treatment for a preselected period; and
  (xv) that the prescriber understands that the patient and the prescriber will be automatically enrolled in the registry.

10. The computer-implemented method of claim 1 or 2, further comprising the centralized administration system assigning, responsive to the authorization or reauthorization of the patient, a case manager to the patient.

11. The computer-implemented method of claim 1 or 2, further comprising the centralized administration system matching, responsive to the authorization or reauthorization of the patient, the patient to an authorized treatment site or confirming that a treatment site to which the prescriber referred the patient is an authorized treatment site.

12. The computer-implemented method of claim 1 or 2, further comprising the central administration system communicating data indicating verification of patient enrollment in the central administration system and authorization or reauthorization of the patient for treatment with natalizumab to the prescriber and/or the authorized treatment site before the processing at the authorized treatment site.

13. The computer-implemented method of claim 1 or 2, further comprising the database storing an indication that the prescriber has been trained on known risks, potential benefits, and appropriate use of natalizumab.

14. The computer-implemented method of claim 1 or 2, further comprising the database storing an indication that one or more healthcare providers at the authorized treatment site have been trained on known risks, potential benefits, and appropriate use of natalizumab.

15. The computer-implemented method of claim 1 or 2, wherein the treatment site checklist indicates that each of the authorized treatment sites must investigate the following, for each patient to be treated at the authorized treatment site:
  (i) over the past month, has the patient had any new or worsening medical problems that have persisted over several days;
  (ii) does the patient have a medical condition that can weaken the immune system; and
  (iii) does the patient report receiving any concurrent immunomodulatory or immunosuppressant therapies, or steroid use.

16. The computer-implemented method of claim 1 or 2, further comprising the centralized administration system permitting treatment with natalizumab, wherein natalizumab is administered at the authorized treatment site only if each of the following criteria is met:
  (i) presence of a current authorization form within the current authorization period;

(ii) absence of a notice of discontinuation in connection with an identifier for a patient to be treated, unless a subsequent re-enrollment has occurred;
(iii) absence of any new or worsening medical problems that have persisted over several days in the patient to be treated;
(iv) absence of a medical condition that can weaken the immune system in the patient to be treated; and
(v) absence of any medications to treat cancer or multiple sclerosis or any other medications that weaken the immune system in the patient to be treated; and
(vi) absence of any one of Solu-Medrol®, methylprednisolone, Decadron®, dexamethasone, Depo-Medrol®, prednisone, or other steroid medicines within the past month in the patient to be treated.

17. The computer-implemented method of claim 1 or 2, wherein the anti-VLA-4 antibody is administered intravenously on a monthly basis to each patient to be treated.

18. The computer-implemented method of claim 1 or 2, wherein the contraindicated treatment comprises one or more of a steroid therapy, an immunomodulatory therapy, or an immunosuppressant therapy.

19. The computer-implemented method of claim 1 or 2, further comprising, for each patient for which a prescriber for that patient has prescribed treatment with natalizumab and an authorized treatment site for that patient at which the prescribed treatment is to be administered, the centralized administration system actively querying one or both of the prescriber and the authorized treatment site at a regular interval regarding the occurrence of PML or death in the patient treated with natalizumab.

20. The computer-implemented method of claim 19, wherein the regular interval is every 2, 3, 4, 5, 6, 8, 10 or 12 months.

21. The computer-implemented method of claim 1 or 2, further comprising the distributed system tracking administration of natalizumab to at least 10,000 patients.

* * * * *